(12) United States Patent
Morgan et al.

(10) Patent No.: US 12,178,522 B2
(45) Date of Patent: Dec. 31, 2024

(54) VERSATILE TRACKING ARRAYS FOR A NAVIGATION SYSTEM AND METHODS OF RECOVERING REGISTRATION USING THE SAME

(71) Applicant: MAKO Surgical Corp., Weston, FL (US)

(72) Inventors: Jonathan Mark Morgan, Biscayne Park, FL (US); Jean Gonzalez, Plantation, FL (US)

(73) Assignee: MAKO Surgical Corp., Weston, FL (US)

( * ) Notice: Subject to any disclaimer, the term of this patent is extended or adjusted under 35 U.S.C. 154(b) by 478 days.

(21) Appl. No.: 17/453,006

(22) Filed: Nov. 1, 2021

(65) Prior Publication Data
US 2022/0047335 A1 Feb. 17, 2022

Related U.S. Application Data

(63) Continuation of application No. 16/422,007, filed on May 24, 2019, now Pat. No. 11,191,594.
(Continued)

(51) Int. Cl.
*A61B 34/20* (2016.01)
*A61B 17/88* (2006.01)
(Continued)

(52) U.S. Cl.
CPC .............. *A61B 34/20* (2016.02); *A61B 17/88* (2013.01); *A61B 34/30* (2016.02);
(Continued)

(58) Field of Classification Search
CPC ............ A61B 34/20; A61B 2034/2055; A61B 2034/2057
See application file for complete search history.

(56) References Cited

U.S. PATENT DOCUMENTS 5,249,581 A 10/1993 Horbal et al.
5,279,309 A 1/1994 Taylor et al.
(Continued)

FOREIGN PATENT DOCUMENTS

WO 2016044934 A1 3/2016
WO 2016118744 A1 7/2016
(Continued)

OTHER PUBLICATIONS

Semple, Mark et al., "Design of a Flexible Optical Tracker for Orthopaedic Navigation", University of British Columbia, 2015, 10 pages.
(Continued)

*Primary Examiner* — Zade Coley
(74) *Attorney, Agent, or Firm* — Howard & Howard Attorneys PLLC

(57) ABSTRACT

A navigation system includes a first and second tracker supports independently affixed to a rigid object and separated by a distance. A first plurality of trackable elements are secured to the first tracker support and a second plurality of trackable elements are secured to the second tracker support. A localizer tracks the trackable elements and controller(s) define a tracking arrangement to be tracked based on a combination of the first and second plurality of trackable elements. A geometry of the tracking arrangement is registered relative to the rigid object and the controller(s) track the rigid object by detecting the registered geometry. The controller(s) identify a condition wherein at least one trackable element has been displaced relative to the registered geometry, and in response, generate an instruction to a manipulator controller to interrupt operation of a robotic manipulator.

13 Claims, 10 Drawing Sheets

Related U.S. Application Data

(60) Provisional application No. 62/792,147, filed on Jan. 14, 2019, provisional application No. 62/676,497, filed on May 25, 2018.

(51) Int. Cl.
*A61B 34/30* (2016.01)
*A61B 17/56* (2006.01)
*A61B 17/84* (2006.01)
*A61B 34/00* (2016.01)
*A61B 90/00* (2016.01)

(52) U.S. Cl.
CPC ....... *A61B 2017/564* (2013.01); *A61B 17/846* (2013.01); *A61B 2034/2055* (2016.02); *A61B 2034/252* (2016.02); *A61B 2090/364* (2016.02); *A61B 2090/3916* (2016.02); *A61B 2090/3945* (2016.02); *A61B 2090/3983* (2016.02); *A61B 2090/3991* (2016.02)

(56) References Cited

U.S. PATENT DOCUMENTS

| | | | |
|---|---|---|---|
| 5,408,409 A * | 4/1995 | Glassman | G05B 19/4099 |
| | | | 600/407 |
| 5,676,673 A | 10/1997 | Ferre et al. | |
| 6,061,644 A | 5/2000 | Leis | |
| 6,167,145 A | 12/2000 | Foley et al. | |
| 6,231,526 B1 | 5/2001 | Taylor et al. | |
| 6,236,875 B1 | 5/2001 | Bucholz et al. | |
| 6,282,437 B1 | 8/2001 | Franck et al. | |
| 6,347,240 B1 | 2/2002 | Foley et al. | |
| 6,430,434 B1 | 8/2002 | Mittelstadt | |
| 6,711,431 B2 * | 3/2004 | Sarin | A61F 2/4657 |
| | | | 606/130 |
| 6,714,629 B2 | 3/2004 | Vilsmeier | |
| 6,827,723 B2 | 12/2004 | Carson | |
| 6,856,828 B2 * | 2/2005 | Cossette | A61B 90/39 |
| | | | 600/429 |
| 6,877,239 B2 | 4/2005 | Leitner et al. | |
| 6,923,817 B2 | 8/2005 | Carson et al. | |
| RE39,133 E | 6/2006 | Clayton et al. | |
| 7,237,556 B2 | 7/2007 | Smothers et al. | |
| 7,477,926 B2 | 1/2009 | McCombs | |
| 7,535,411 B2 | 5/2009 | Falco | |
| 7,547,307 B2 | 6/2009 | Carson et al. | |
| 7,668,584 B2 | 2/2010 | Jansen | |
| 7,696,899 B2 | 4/2010 | Immerz et al. | |
| 7,725,162 B2 | 5/2010 | Malackowski et al. | |
| 7,751,865 B2 | 7/2010 | Jascob et al. | |
| 7,780,681 B2 | 8/2010 | Sarin et al. | |
| RE42,194 E | 3/2011 | Foley et al. | |
| RE42,226 E | 3/2011 | Foley et al. | |
| 8,046,053 B2 | 10/2011 | Foley et al. | |
| 8,068,648 B2 | 11/2011 | DiSilvestro et al. | |
| 8,126,535 B2 | 2/2012 | Maier et al. | |
| 8,290,570 B2 | 10/2012 | Hoppe et al. | |
| 8,311,611 B2 | 11/2012 | Csavoy et al. | |
| 8,340,751 B2 | 12/2012 | Markowitz et al. | |
| 8,357,165 B2 | 1/2013 | Grant et al. | |
| 8,494,614 B2 | 7/2013 | Markowitz et al. | |
| 8,548,565 B2 | 10/2013 | Hunter et al. | |
| 8,750,965 B2 | 6/2014 | Woerlein et al. | |
| 9,008,757 B2 | 4/2015 | Wu | |
| 9,119,655 B2 | 9/2015 | Bowling et al. | |
| 9,436,993 B1 | 9/2016 | Stolka et al. | |
| 9,579,161 B2 | 2/2017 | Hartmann et al. | |
| 9,622,824 B2 | 4/2017 | Goldbach | |
| 9,707,043 B2 | 7/2017 | Bozung | |
| 9,713,506 B2 | 7/2017 | Fanson et al. | |
| 9,724,165 B2 | 8/2017 | Arata et al. | |
| 9,730,680 B2 | 8/2017 | Tuma et al. | |
| 9,795,394 B2 | 10/2017 | Bonutti | |
| 9,974,625 B2 | 5/2018 | Fleck et al. | |
| 9,987,093 B2 | 6/2018 | Christian et al. | |
| 10,010,381 B2 * | 7/2018 | Hodgson | A61B 90/39 |
| 10,080,616 B2 | 9/2018 | Wilkinson et al. | |
| 10,092,305 B2 | 10/2018 | Dardenne et al. | |
| 10,117,748 B2 | 11/2018 | Fanson et al. | |
| 2002/0133175 A1 | 9/2002 | Carson | |
| 2002/0198451 A1 | 12/2002 | Carson | |
| 2003/0069591 A1 | 4/2003 | Carson et al. | |
| 2003/0187351 A1 | 10/2003 | Franck et al. | |
| 2004/0010190 A1 * | 1/2004 | Shahidi | A61B 34/70 |
| | | | 600/407 |
| 2004/0068263 A1 * | 4/2004 | Chouinard | A61B 90/10 |
| | | | 606/86 R |
| 2005/0075632 A1 | 4/2005 | Russell et al. | |
| 2005/0245820 A1 * | 11/2005 | Sarin | A61B 5/064 |
| | | | 600/429 |
| 2006/0142657 A1 * | 6/2006 | Quaid | A61B 90/37 |
| | | | 600/424 |
| 2007/0049819 A1 | 3/2007 | Stifter et al. | |
| 2007/0081695 A1 | 4/2007 | Foxlin et al. | |
| 2007/0239169 A1 | 10/2007 | Plaskos et al. | |
| 2007/0270685 A1 * | 11/2007 | Kang | A61B 34/30 |
| | | | 600/424 |
| 2008/0154127 A1 | 6/2008 | DiSilvestro et al. | |
| 2009/0099445 A1 | 4/2009 | Burger | |
| 2009/0143670 A1 | 6/2009 | Daigneault | |
| 2009/0281417 A1 * | 11/2009 | Hartmann | A61B 34/20 |
| | | | 600/424 |
| 2010/0030232 A1 | 2/2010 | Zehavi et al. | |
| 2011/0004224 A1 | 1/2011 | Daigneault et al. | |
| 2011/0263971 A1 | 10/2011 | Nikou et al. | |
| 2013/0190887 A1 | 7/2013 | Fanson et al. | |
| 2013/0345718 A1 * | 12/2013 | Crawford | A61B 90/39 |
| | | | 606/130 |
| 2014/0200621 A1 * | 7/2014 | Malackowski | A61B 34/70 |
| | | | 606/86 R |
| 2014/0253712 A1 | 9/2014 | Vilsmeier et al. | |
| 2014/0276001 A1 | 9/2014 | Ungi et al. | |
| 2014/0330114 A1 | 11/2014 | Navab | |
| 2015/0209119 A1 | 7/2015 | Theodore et al. | |
| 2015/0338214 A1 | 11/2015 | Uhde et al. | |
| 2016/0038249 A1 * | 2/2016 | Arata | A61B 34/10 |
| | | | 703/11 |
| 2016/0196666 A1 | 7/2016 | Venkatraghavan et al. | |
| 2016/0199148 A1 | 7/2016 | Maracaja-Neto | |
| 2016/0249988 A1 | 9/2016 | Pfeifer et al. | |
| 2016/0256225 A1 | 9/2016 | Crawford et al. | |
| 2016/0296293 A1 | 10/2016 | Gill et al. | |
| 2016/0296296 A1 * | 10/2016 | Bowling | A61B 34/32 |
| 2016/0302870 A1 | 10/2016 | Wilkinson et al. | |
| 2016/0343273 A1 * | 11/2016 | Stuart | B25J 9/1676 |
| 2016/0354153 A1 * | 12/2016 | Hodgson | A61B 90/39 |
| 2017/0069073 A1 | 3/2017 | Sela et al. | |
| 2017/0172669 A1 | 6/2017 | Berkowitz et al. | |
| 2017/0224437 A1 | 8/2017 | Fleck et al. | |
| 2017/0245944 A1 | 8/2017 | Crawford et al. | |
| 2017/0252114 A1 | 9/2017 | Crawford et al. | |
| 2017/0340395 A1 | 11/2017 | Perez | |
| 2017/0348061 A1 | 12/2017 | Joshi et al. | |
| 2017/0360515 A1 | 12/2017 | Kozak et al. | |
| 2018/0185113 A1 | 7/2018 | Gregerson et al. | |
| 2018/0193097 A1 | 7/2018 | McLachlin et al. | |
| 2018/0200001 A1 | 7/2018 | Erbe | |
| 2018/0256282 A1 * | 9/2018 | Hodgson | A61B 90/39 |
| 2018/0317803 A1 | 11/2018 | Ben-Yishai et al. | |
| 2018/0333214 A1 | 11/2018 | Han et al. | |
| 2019/0000372 A1 | 1/2019 | Gullotti et al. | |
| 2019/0021798 A1 | 1/2019 | Netravali et al. | |
| 2019/0038362 A1 * | 2/2019 | Nash | A61B 34/25 |
| 2019/0099222 A1 | 4/2019 | Nahum et al. | |
| 2019/0357986 A1 | 11/2019 | Morgan et al. | |

FOREIGN PATENT DOCUMENTS

| | | |
|---|---|---|
| WO | 2017087371 A1 | 5/2017 |
| WO | 2017200446 A1 | 11/2017 |

(56) References Cited

FOREIGN PATENT DOCUMENTS

| WO | 2018202529 A1 | 11/2018 |
| WO | 2019108925 A1 | 6/2019 |

OTHER PUBLICATIONS

Semple, Mark, "Implementation and Verification of a Flexible Optical Tracker", The University of British Columbia, Feb. 2015, 152 pages.

\* cited by examiner

VERSATILE TRACKING ARRAYS FOR A NAVIGATION SYSTEM AND METHODS OF RECOVERING REGISTRATION USING THE SAME

CROSS-REFERENCE TO RELATED APPLICATIONS

The subject application is a continuation of U.S. Nonprovisional patent application Ser. No. 16/422,007, filed May 24, 2019, which claims the benefit of U.S. Provisional Patent App. No. 62/676,497, filed May 25, 2018, and which claims the benefit of U.S. Provisional Patent App. No. 62/792,147, filed Jan. 14, 2019, the disclosures of each of the aforementioned applications being hereby incorporated by reference in their entirety.

TECHNICAL FIELD

The present disclosure relates generally to tracking an object using a versatile tracking array defined by the combined geometry of separate trackers attached to the same object and techniques for interrupting operation of a robotic manipulator in response to detecting registration loss of the versatile tracking array.

BACKGROUND

Navigation systems assist users in precisely locating objects. For instance, navigation systems are used in industrial, aerospace, and medical applications. In the medical field, navigation systems assist surgeons in precisely placing surgical instruments relative to a target site in a patient, for example, during a surgical operation. The target site usually requires some form of treatment, such as tissue removal. Conventional navigation systems employ a localizer including one or more imaging technologies that cooperate with trackers to provide position and/or orientation data associated with the surgical instrument and the target site, e.g., the volume of bone to be removed. These trackers allow a surgeon to see the position and/or orientation of the surgical tool overlaid on a monitor in conjunction with a preoperative or an intraoperative image of the patient. The preoperative images may be generated by Mill, CT scans, or other well-known medical imaging technologies, prior to beginning the surgical operation.

The localizer is usually placed so that it has a field of view of the trackers, that is, the localizer is positioned so that the target site of the patient is within the target space of the localizer. The trackers include identifiable arrays of fiducials that are fixed to a surgical instrument or to a patient to move in concert with the surgical instrument or the patient, respectively. From the detected position of the trackers, the surgical navigation system can determine the position and/or orientation of the surgical tool or patent anatomy, and monitor and track the position and/or orientation for changes over time. The term position refers to the three-dimensional coordinate values relative to the surgical navigation system. The term orientation refers to the pitch, roll and yaw relative to the surgical navigation system or to a reference orientation defined for the object. Collectively, the position and the particular pitch, roll, and yaw values of a given orientation may be referred to as the object's pose. When both the position and orientation (or pose) are defined, the object is known and trackable to the surgical navigation system.

The tracker attached to the patient is often rigidly secured to the bone being treated, thereby maintaining a fixed relationship with respect to the target site owing to the rigid nature of the bone, the rigid structure of the tracker and the fixed securement therebetween. In addition to the trackers themselves being secured to the bone being treated, a further checkpoint screw is typically required. Using a reference tracking array placed into contact with the checkpoint screw, and measuring the relative position of the checkpoint to the tracker affixed to the bone, an operator can confirm the registration of the tracker to the bone and ensure that the mounting of the tracker to the bone remains true. Periodically performing this check during the operation can increase the total time required for the operation. By using separate trackers on the surgical instrument and the patient, the treatment end of the surgical instrument can be precisely positioned at the target site by the surgeon aided by the navigation system.

During an initial phase of the operation, an object, whether a surgical tool or a patient's anatomy, must be calibrated or registered to the surgical navigation system. The process of calibration, or registration, refers to establishing a relationship between a physical object and its tracker to the virtual representations of the object and tracker as data within the surgical navigation system, that is, as virtual object data and virtual tracker data, respectively. For example, preoperative imaging of a patient's anatomy may be used to generate a 3D model of that anatomy as virtual object data in the memory and virtual environment of the surgical navigation system. Likewise, a surgical tool may be manufactured according to known geometry and structure. This geometry and structure may be represented in a 3D model of that tool as virtual object data in the memory and virtual environment of the surgical navigation system. To perform the calibration, additional reference pointers or frames having additional tracker fiducial arrays may be required to touch off reference points according to a registration sequence.

Trackers, adapted for attachment to a patient's anatomy for use during navigation-guided surgery, typically include two or more bone pins affixed to a bone in close proximity. Placing multiple bone pins in close proximity may require a single large incision much greater than the size of the bone pin itself. A clamp is secured to the bone pins, which also provides an interface for an array adapter. The array adapter may provide rotational adjustments to allow the tracker to be precisely arranged relative to the patient's anatomy and the localizer. The array adapter attaches to and supports the array frame. The frame is typically an expanded square, rectangular, diamond, or other geometric structure. The frame supports the reflective or emissive markers that focuses or provides the signals in a wavelength suitable for the sensor technology included in the localizer. The markers are typically arranged on the frame to maximize the distance between markers, such as at the corners of a square or rectangular frame.

The accuracy of the navigation tracking is limited by the sensitivity of the imaging technology and the ability to relate the location of each marker relative to the other markers. Improving the quality of the tracking requires greater distance between the markers. On conventional trackers, this leads to ever larger frame components. Supporting larger tracker frames may thus require larger bone pins or potential bone damage as larger masses are cantilevered off bone tissue.

Therefore, there is a need in the art for improved trackers and methods that address the desire for improved accuracy while minimizing invasion into tissue and bone during robotic surgery.

SUMMARY

This Summary introduces a selection of concepts in a simplified form that are further described below in the Detailed Description. This Summary is not intended to limit the scope of the claimed subject matter, and does not necessarily identify each and every key or essential feature of the claimed subject matter.

In a first aspect, a method is provided for operating a navigation system usable with a robotic manipulator and a manipulator controller configured to control the robotic manipulator, the navigation system comprising a first tracker support affixed to a rigid object and a first plurality of trackable elements secured to the first tracker support, a second tracker support affixed to the rigid object and a second plurality of trackable elements secured to the second tracker support, the first tracker support and the second tracker support adapted to be independently secured to the rigid object and separated by a distance, the navigation system comprising a localizer configured to track the first and second plurality of trackable elements, the method comprising the navigation system: defining a tracking arrangement to be tracked based on a combination of the first and second plurality of trackable elements; registering a geometry of the tracking arrangement relative to the rigid object; tracking the rigid object by detecting the registered geometry of the tracking arrangement; identifying a condition wherein at least one trackable element has been displaced relative to the registered geometry; and in response to identifying the condition, generating an instruction to the manipulator controller for interrupting operation of the robotic manipulator.

In a second aspect, a navigation system is provided that is usable with a robotic manipulator and a manipulator controller configured to control the robotic manipulator, the navigation system comprising: a first tracker support affixed to a rigid object and a first plurality of trackable elements secured to the first tracker support; a second tracker support affixed to the rigid object and a second plurality of trackable elements secured to the second tracker support; the first tracker support and the second tracker support adapted to be independently secured to the rigid object and separated by a distance; a localizer configured to track the first and second plurality of trackable elements; and at least one controller coupled to the localizer and being configured to: define a tracking arrangement to be tracked based on a combination of the first and second plurality of trackable elements; register a geometry of the tracking arrangement relative to the rigid object; track the rigid object by being configured to detect the registered geometry of the tracking arrangement; identify a condition wherein at least one trackable element has been displaced relative to the registered geometry; and in response to identification of the condition, generate an instruction to the manipulator controller to interrupt operation of the robotic manipulator.

In a third aspect, a method is provided for operating a surgical system comprising navigation system, a robotic manipulator, and a manipulator controller, the navigation system comprising a first tracker support affixed to a rigid object and a first plurality of trackable elements secured to the first tracker support, a second tracker support affixed to the rigid object and a second plurality of trackable elements secured to the second tracker support, the first tracker support and the second tracker support adapted to be independently secured to the rigid object and separated by a distance, the navigation system comprising a localizer configured to track the first and second plurality of trackable elements, the method comprising: defining, with the navigation system, a tracking arrangement to be tracked based on a combination of the first and second plurality of trackable elements; registering, with the navigation system, a geometry of the tracking arrangement relative to the rigid object; tracking, with the navigation system, the rigid object by detecting the registered geometry of the tracking arrangement; controlling, with the manipulator controller, operation of the robotic manipulator; identifying, with the navigation system, a condition wherein at least one trackable element has been displaced relative to the registered geometry; in response to identifying the condition, generating, with the navigation system, an instruction and communicating the instruction to the manipulator controller; and in response to receiving the instruction from the navigation system, interrupting, with the manipulator controller, operation of the robotic manipulator.

BRIEF DESCRIPTION OF THE DRAWINGS

Advantages of the present disclosure will be readily appreciated as the same becomes better understood with reference to the following detailed description when considered in connection with the accompanying drawings, wherein like numbers denote like structures.

DETAILED DESCRIPTION

Figure 1:
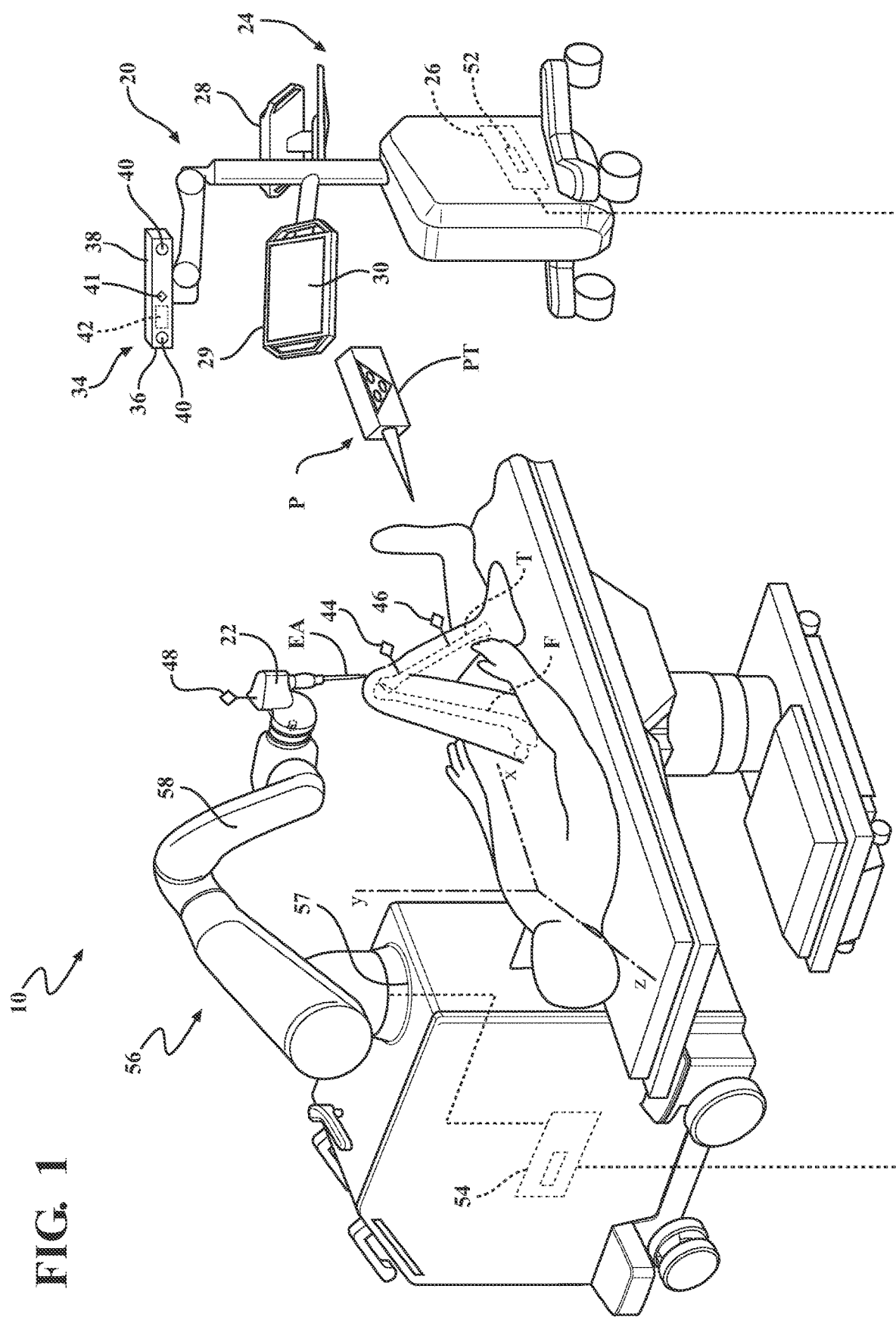
FIG. 1 is a perspective view of a surgical navigation system being used in conjunction with a robotic surgical device.

Referring to FIG. 1, a surgical system 10 is illustrated for performing surgery on a patient. The version shown in FIG. 1 includes a surgical navigation system 20. The surgical navigation system 20 is shown in a surgical setting such as an operating room of a medical facility. The surgical navigation system 20 is set up to track movement of various objects in the operating room. Such objects include, for example, a surgical instrument 22, a femur F of the patient, a tibia T of the patient, and/or a robotic manipulator 56. The surgical navigation system 20 tracks these objects for purposes of displaying their relative positions and orientations to the surgeon and, in some cases, for purposes of controlling or constraining movement of the surgical instrument 22 and/or robotic manipulator 56 relative to virtual cutting boundaries associated, in the illustrated example, with the femur F and tibia T.

The surgical navigation system 20 includes a computer cart assembly 24 that houses a navigation computer 26. A navigation interface is in operative communication with the navigation computer 26. The navigation interface includes a first display 28 adapted to be situated outside of the sterile field and a second display 29 adapted to be situated inside the sterile field. The displays 28, 29 are adjustably mounted to the computer cart assembly 24. First and second input devices (not shown) such as a keyboard and mouse can be used to input information into the navigation computer 26 or otherwise select/control certain aspects of the navigation computer 26. Other input devices are contemplated including a touch screen 30, gesture control, or voice-activation.

A localizer 34 communicates with the navigation computer 26. In the example shown, the localizer 34 is an optical localizer and includes a camera unit 36. The camera unit 36 has an outer casing 38 that houses one or more optical sensors 40. In some examples at least two optical sensors 40 are employed. The optical sensors 40 are capable of variable attenuation of radiant energy, for example, light, into signals as small bursts of electrical current that convey information. The camera unit 36 may also include a video camera 41 or other additional sensing device.

The optical sensors 40 may be separate charge-coupled devices (CCD). In some examples, two, two-dimensional CCDs are employed. In some cases, the optical sensors 40 are arranged for stereoscopic operation, or single cameras combined with depth sensors, laser range finders, and the like, may be used. It should be appreciated that in other examples, separate camera units, each with a separate CCD, or two or more CCDs, could also be arranged around the operating room. The optical sensors 40 may include CCDs capable of detecting infrared (IR) radiant energy. In alternative examples, the optical sensors may employ other sensing technology, including, but not limited to, complimentary metal-oxide semiconductor (CMOS) active-pixel sensors, and the like.

The camera unit 36 may be mounted on an adjustable arm or other articulated support structure of the cart assembly 24 to selectively position the localizer 34 with a, preferably unobstructed, field of view of the target space including the surgical setting within which will be the patient anatomy and trackers, as discussed below. In some examples, the camera unit 36 is adjustable in at least one degree of freedom by rotating about a rotational joint. In other examples, the camera unit 36 is adjustable about two or more degrees of freedom.

The camera unit 36 includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. The connection could also use a company specific protocol. In other examples, the optical sensors 40 may communicate directly with the navigation computer 26, such that the navigation computer incorporates the functionality of, and thus operates as, the camera controller 42. Processing of the signals from the optical sensors 40 may occur at the camera controller 42. Alternatively, the camera controller 42 may communicate the signals to the navigation computer 26 for processing.

The navigation computer 26 can be a personal computer or laptop computer. The navigation computer 26 has the display 28, central processing unit (CPU) and/or other processors, memory (not shown), and storage (not shown). The navigation computer 26 is loaded with software as described below. The software is configured to execute algorithms for performing any of the functionality and steps described herein. The software converts the signals received from the camera unit 36 or the optical sensors 40 into data representative of the position and orientation of the objects being tracked. Position and orientation signals and/or data is used by the navigation computer 26 for purposes of tracking objects. The computer cart assembly 24, display 28, and camera unit 36 may be like those described in U.S. Pat. No. 7,725,162 to Malackowski, et al. issued on May 25, 2010, entitled "Surgery System," hereby incorporated by reference.

The surgical system 10 illustrated in FIG. 1 includes a plurality of tracking devices 44, 46, 48, also referred to herein simply as trackers. In the illustrated example, two trackers 44, 46 are coupled to the tibia T of the patient.

An instrument tracker 48 is coupled to the surgical instrument 22. The instrument tracker 48 may be integrated into the surgical instrument 22 during manufacture or may be separately mounted to the surgical instrument 22 in preparation for the surgical procedure. The working end of the surgical instrument 22, which is being tracked by virtue of the instrument tracker 48, may be an energy applicator EA such as a rotating bur, saw blade, electrical ablation device, or the like. The energy applicator EA may be a separate component such as a replaceable bur, saw blade, ablator, or the like that is releasably connected to a handpiece of the surgical tool 22 or the energy application EA may be integrally formed with the handpiece.

The trackers 44, 46, 48 may be active trackers or passive trackers. In general, any passive or active tracker or marker can be considered a trackable element. The active or passive trackers can have various configurations. The active tracker has its own power source and may be battery powered with an internal battery or may have leads to receive power through the navigation computer 26, which, like the camera unit 36, may receive external power. The active tracker may have an array of fiducials (also referred to as tracking elements or markers) that actively generate and emit radiation in a wavelength detectable by the optical sensors 40. The fiducials of an active tracker may be a light emitting diode (LED), including, for example, an infrared LED. The array of active fiducials may be "always on" or may be operative to selectively fire, that is emit radiation, according to and in response to commands from the surgical navigation system 20. In such selective-fire active trackers, the tracker may communicate by way of a wired or a wireless connection with the navigation computer 26 of surgical navigation system 20. Other examples of active trackers are contemplated, such as other type of optical elements besides LEDs, electromagnetic trackers, radio frequency trackers, or any other type of tracker whereby a power source on the tracker can energize an element that can be detected by the navigation system (using optical sensing or any other modality).

Additionally or alternatively, the tracker may include passive trackers or markers. Unlike the active tracker, the passive tracker array does not require a power source. In one example, passive trackers focus or reflect ambient radiation or radiation that has been emitted into the target space, for example by one or more infrared LEDs provided on the camera unit 36 or elsewhere associated with the surgical system 10. The passive trackers or markers may have various configurations. The passive trackers may be optical or non-optical. For example, non-optical passive trackers may include passive electromagnetic trackers, passive radio frequency trackers, or any other type of passive element that can reflect or radiate a signal back to the navigation system (using any modality). In other examples, the passive markers can be unique shapes, patterns, barcodes, etc., that can be optically identified by the navigation system, e.g., using machine vision. Any of the techniques, trackers, or system examples described herein may utilize any combination and configuration of active and passive trackers In the example shown, the surgical instrument 22 is attached to a surgical manipulator 56. Such an arrangement is shown in U.S. Pat. No. 9,119,655 to Bowling et al, issued Sep. 1, 2015, entitled, "Surgical Manipulator Capable of Controlling a Surgical Instrument in Multiple Modes," the disclosure of which is hereby incorporated by reference.

In other examples, the surgical instrument 22 may be manually positioned by only the hand of the user, without the aid of any cutting guide, jig, or other constraining mechanism such as a manipulator or robot. Such a surgical instrument is described in U.S. Pat. No. 9,707,043 to Bozung et al., issued Jul. 18, 2017, the disclosure of which is hereby incorporated by reference.

Initially, the objects to be located are viewed by the optical sensors 40 and identified. The objects may be identified by selecting the objects to be tracked using an input device connected to the machine vision controller 14 or navigation computer 26. The navigation computer 26 may store detailed information regarding numerous objects in memory or data storage on the navigation computer 26 and the user may be able to manually select the objects to be tracked from a database of objects. Although described generally herein with regard to trackers attached to a patient's anatomy, for example, a bone, the present disclosure contemplates that objects beyond anatomical objects may be tracked. Surgical tools, reference frames, robotic manipulators or other objects may be tracked using the systems and methods as disclosed herein.

Using the disclosed systems and methods, an operator may desire to define a volume to be tracked that is not limited to the physical boundaries of a particular item. The operator may desire to define an additional margin of space around an item to be avoided, for example, where a robotic manipulator 56 is in use. The navigation computer 26 may present a visual interface to allow the operator to designate which markers define the tracker and allow the operator to designate the object, including in some cases a specified volume in space, to be tracked.

Additionally, or alternatively, the navigation computer 26 may identify the objects to be tracked based on a pre-operative surgical plan. In this case, the navigation computer 26 may have a preset list of workflow objects that may be used in the pre-scripted surgical workflow. The navigation computer 26 may actively search for and locate the workflow objects using software. For instance, groups of pixels associated with different sizes and shapes of the various objects may be stored in the navigation computer 26. By selecting/identifying the objects to be located/tracked, the software identifies the corresponding group of pixels and the software then operates to detect like groups of pixels using conventional pattern recognition technology.

Additionally, or alternatively, the objects to be located/tracked can be identified using an interface in which one of the operators outlines or selects the objects to be tracked on one or more of the displays 28, 29. For instance, images taken by the optical sensors 40, or video camera 41, of the surgical site may be displayed on one or more of the displays 28, 29 (and/or other displays). The operator then, using a mouse, digital pen, or the like, traces objects to be located/tracked on the display 28 and/or 29. The software stores the pixels associated with the object that was traced into its memory. The operator (or other user) may identify each object by a unique identifier such as naming the object using the software so that the saved group of pixels may be associated with the unique identifier. Multiple objects could be stored in this manner.

The navigation computer 26 utilizes conventional pattern recognition and associated software to later detect these objects. The navigation system 20 is able to detect movement of these objects by continuously taking images, reviewing the images, and detecting movement of the groups of pixels associated with the objects.

Further, in addition or in the alternative, the object to be located/tracked can be identified through recognition of the object, or the tracker or trackers attached to the object. The particular configuration of the markers on the tracker can be sufficient to identify to the navigation computer 26 the object of interest when that configuration is compared against stored tracker information. In a particular example, the linear distance between markers may be measurable by the navigation computer 26 and sufficient to identify tracker to the navigation computer 26. In this example, two trackers each having two markers can differentiate between two objects based on two different separation distances between the markers on the respective trackers. Other characteristic configurations that may enable this identification include the size of markers, shape, color or other patterns.

In conventional surgical navigation systems, the objects to be tracked are initially located and registered using a navigation pointer P. For example, the navigation pointer P may have an integrated tracker PT. The navigation computer 26 may store initial data corresponding to a location of the tip of the pointer P relative to the tracker PT such that the navigation system 20 is able to locate and track the tip of the pointer P in the localizer coordinate system LCLZ. Accordingly, prior to the start of the surgical procedure, once all the objects are located in their desired locations, one of the participants may touch all of the objects with the pointer P, while identifying the objects in the navigation system 20 using one of the input devices described above. So, for example, when the participant touches the surgical instrument 22 with the tip of the pointer P, the participant may simultaneously trigger collection of that point in the localizer coordinate system LCLZ (via another input device, such as a foot pedal). When the point is collected, the participant can also enter into the navigation software the identity of the object (via typing, pull-down selection from a list of objects, etc.).

Figure 2:
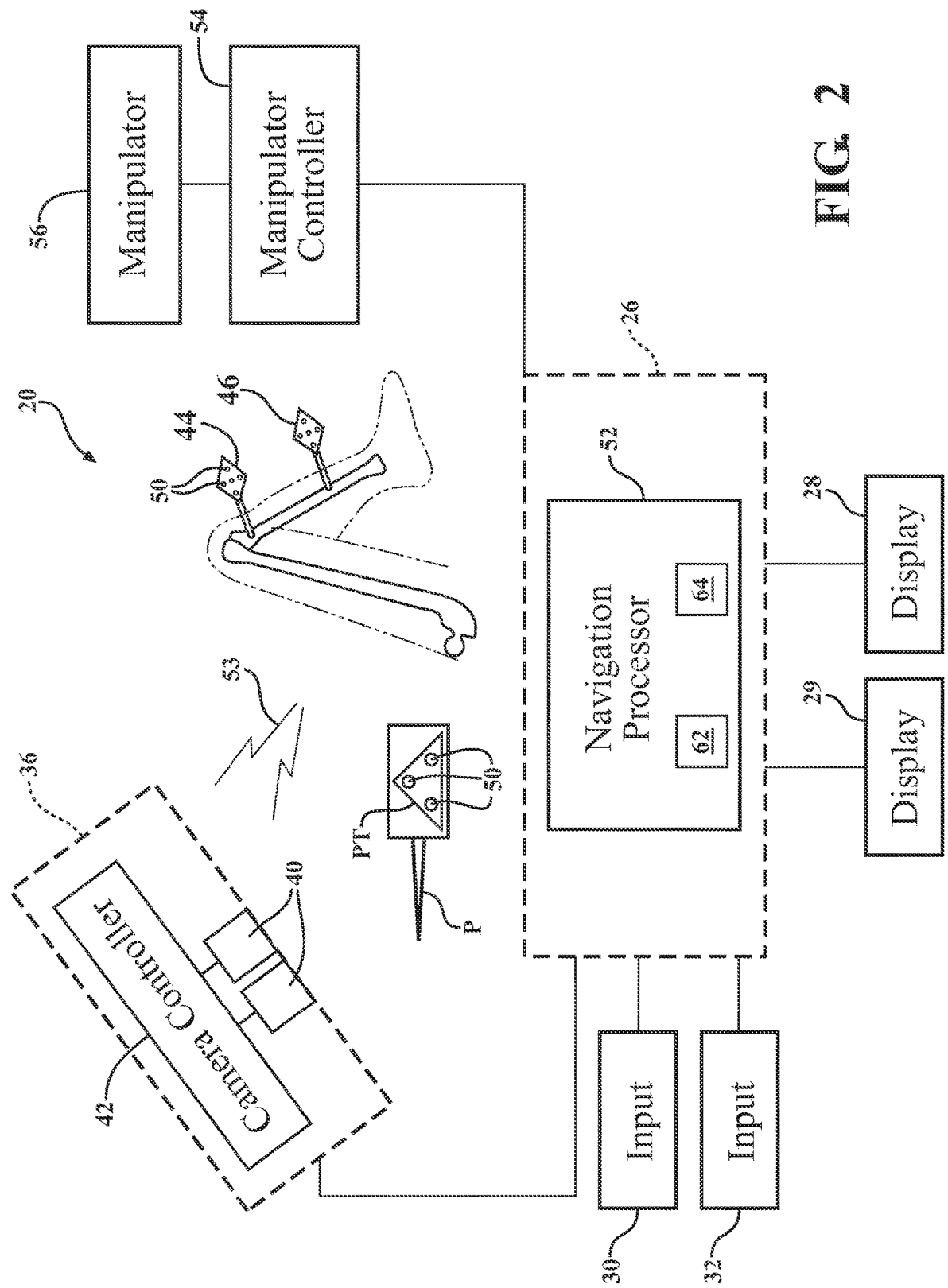
FIG. 2 is a schematic view of a control system for controlling the surgical navigation system and robotic surgical device.

Referring to FIG. 2, a schematic view of a control system for controlling the surgical navigation system 20 and robotic surgical device 56 is shown. In some examples the trackers 44, 46 include fiducials that are connected to a tracker controller (not shown) located in a housing (not shown) of the associated tracker 44, 46 that transmits/receives data to/from the navigation computer 26. In one example, the tracker controllers transmit data through wired connections with the navigation computer 26. In other examples, a wireless connection may be used. In these examples, the navigation computer 26 has a transceiver (not shown) to receive the data from the tracker controller. In other examples, the trackers 44, 46 may have passive markers 50, such as reflectors that reflect light, for example, light emitted by an LED provided on camera unit 36 light. For example, the camera unit 36 may include complementary emitters in a wavelength to which the optical sensors 40 are sensitive. The reflected light is then received by the optical sensors 40. In some examples, the trackers 44, 46 may also include a gyroscope sensor 60 and accelerometer 70, such as the trackers shown in U.S. Pat. No. 9,008,757 to Wu, et al., issued on Apr. 14, 2015, entitled, "Navigation System Including Optical and Non-Optical Sensors," the entire disclosure of which is hereby incorporated by reference. These additional sensors 60, 70, may provide information to the navigation computer 26 for use by the navigation computer to determine or track the trackers' 44, 46 position or orientation.

The navigation computer 26 includes a navigation processor 52. It should be understood that the navigation processor 52 could include one or more processors to control operation of the navigation computer 26. The processors can be any type of microprocessor or multi-processor system. The term "processor" is not intended to limit the scope of the invention to a single processor.

As illustrated in FIG. 2, the camera unit 36 receives optical signals 53 from the fiducials 50 of the trackers 44, 46 and outputs to the processor 52 signals relating to the position of the fiducials 50 of the trackers 44, 46 relative to the localizer 34. Based on the received optical (or non-optical signals, in some examples), navigation processor 52 generates data indicating the relative positions and orientations of the trackers 44, 46, 48 relative to the localizer 34.

Prior to the start of the surgical procedure, additional data are loaded into the navigation processor 52. Based on the position and orientation of the trackers 44, 46, 48 and the previously loaded data, such as virtual object data representing the geometry of the object to which the tracker is attached, navigation processor 52 determines the position of the working end of the surgical instrument 22 (e.g., the centroid of a surgical bur) and the orientation of the surgical instrument 22 relative to the tissue against which the working end is to be applied. In some examples, navigation processor 52 forwards this data to a manipulator controller 54. The manipulator controller 54 can then use the data to control a robotic manipulator 56 as described in U.S. Pat. No. 9,119,655 to Bowling, et al., incorporated above.

The navigation processor 52 also generates image signals that indicate the relative position of the surgical instrument working end to the tissue. These image signals are applied to the displays 28, 29. Displays 28, 29, based on these signals, generate images that allow the surgeon and staff to view the relative position of the surgical instrument working end to the surgical site. The displays, 28, 29, as discussed above, may include a touch screen 30 or other input/output device that allows entry of commands.

In the example shown in FIG. 1, the surgical tool 22 forms part of an end effector of the manipulator 56. The manipulator 56 has a base 57, a plurality of links 58 extending from the base 57, and a plurality of active joints (not numbered) for moving the surgical tool 22 with respect to the base 57. The links 58 may form a serial arm structure as shown in FIG. 1, a parallel arm structure (shown for example in FIG. 3), or other suitable structure. The manipulator 56 has the ability to operate in a manual mode in which a user grasps the end effector of the manipulator 56 in order to cause movement of the surgical tool 22 (e.g., directly, through force/torque sensor measurements that cause active driving of the manipulator 56, or otherwise) or a semi-autonomous mode in which the surgical tool 22 is moved by the manipulator 56 along a predefined tool path (e.g., the active joints of the manipulator 56 are operated to move the surgical tool 22 without requiring force/torque on the end effector from the user). An example of operation in a semi-autonomous mode is described in U.S. Pat. No. 9,119,655 to Bowling, et al., incorporated above. A separate tracker (not shown) may be attached to the base 57 of the manipulator 56 to track movement of the base 57.

The manipulator controller 54 may have a central processing unit (CPU) and/or other manipulator processors, memory (not shown), and storage (not shown). The manipulator controller 54, also referred to as a manipulator computer, is loaded with software as necessary to control and operate the manipulator. The manipulator processors could include one or more processors to control operation of the manipulator 56. The manipulator 56 may be in the form of a conventional robotic system or other conventional machining apparatus, and thus the components thereof shall not be described in detail.

The manipulator controller 54 determines the desired location to which the surgical tool 22 should be moved. Based on this determination, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers (not shown) (e.g., one for controlling each motor) that control the active joints of the manipulator 56 to move the plurality of links 58 and thereby move the surgical tool 22 from the current location to the desired location.

Figure 3:
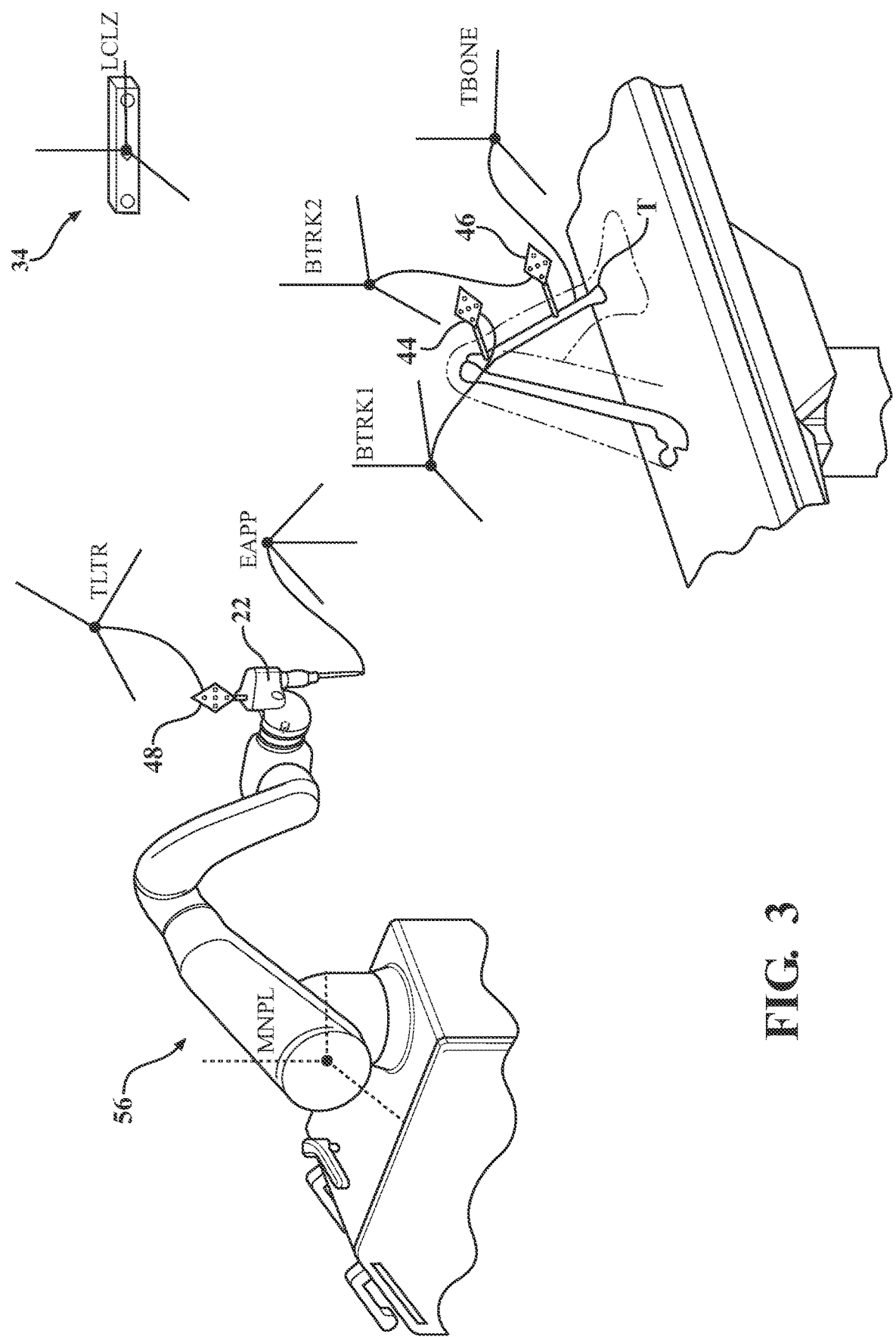
FIG. 3 is a perspective view of coordinate systems used by a surgical navigation system in conjunction with an alternative robotic surgical system.

Referring to FIG. 3, tracking of objects is generally conducted with reference to a localizer coordinate system LCLZ. The localizer coordinate system has an origin and an orientation (a set of x-, y-, and z-axes). During the procedure, one goal is to keep the localizer coordinate system LCLZ in a known position. An accelerometer (not shown) mounted to the camera unit 36 may be used to track sudden or unexpected movement of the localizer coordinate system LCLZ, as may occur when the camera unit 36 is inadvertently bumped by surgical personnel.

Each tracker and object being tracked also has its own coordinate system separate from localizer coordinate system LCLZ. Components of the navigation system 20 that have their own coordinate systems are the bone trackers 44 and 46, and the instrument tracker 48. These coordinate systems are represented as, respectively, bone tracker coordinate systems BTRK1 and BTRK2, and instrument tracker coordinate system TLTR.

Navigation system 20, through the localizer 34 monitors the positions of the tibia T of the patient by monitoring the position of bone trackers 44, 46 coupled to the bone. The tibia coordinate system is TBONE, which are the coordinate systems of the bone to which the trackers 44, 46 are coupled.

Prior to the start of the procedure, pre-operative images of the tibia T are generated (or of other tissues in other examples). These images may be based on MRI scans, radiological scans or computed tomography (CT) scans of the patient's anatomy. These images are mapped to the tibia coordinate system TBONE using well known methods in the art. These images are fixed in the tibia coordinate system TBONE. As an alternative to taking pre-operative images, plans for treatment can be developed in the operating room (OR) from kinematic studies, bone tracing, and other methods. In one example, the other methods may include morphed generic or statistical models.

During an initial phase of the procedure, the bone trackers 44, 46 are coupled to the bones of the patient. The pose (position and orientation) of coordinate system TBONE must be mapped to coordinate systems BTRK1 and BTRK2, respectively. Given the fixed relationship between the bones and their bone trackers 44, 46, positions and orientations of the tibia T in the tibia coordinate system TBONE must be transformed to the bone tracker coordinate systems BTRK1 and BTRK2 so the camera unit 36 is able to track the tibia T by tracking the bone trackers 44, 46. This pose-describing data are stored in memory integral with both manipulator controller 54 and navigation processor 52.

The working end of the surgical instrument 22 (also referred to as energy applicator distal end) has its own coordinate system EAPP. The origin of the coordinate system EAPP may represent a centroid of a surgical cutting bur, for example. The pose of coordinate system EAPP must be fixed to the pose of instrument tracker coordinate system TLTR before the procedure begins. Accordingly, the poses of these coordinate systems EAPP, TLTR relative to each other must be determined in the navigation computer 26. The pose-describing data are stored in memory integral with both manipulator controller 54 and navigation processor 52.

Referring back to FIG. 2, a localization engine 62 is a software module that may be included within the navigation system 20. Components of the localization engine 62 may execute on navigation processor 52. In some examples, however, the localization engine 62 may execute on the manipulator controller 54.

Localization engine 62 receives as inputs the optically-based signals from the camera controller 42 and, in some examples, the non-optically based signals from the tracker controller. Based on these signals, localization engine 62 determines the pose of the bone tracker coordinate systems BTRK1 and BTRK2 in the localizer coordinate system LCLZ. Based on the same signals received for the instrument tracker 48, the localization engine 62 determines the pose of the instrument tracker coordinate system TLTR in the localizer coordinate system LCLZ.

The localization engine 62 forwards the signals representative of the poses of trackers 44, 46, 48 to a coordinate transformer 64. Coordinate transformer 64 is a navigation system software module that runs on navigation processor 52. Coordinate transformer 64 references the data that defines the relationship between the pre-operative images of the patient and the bone trackers 44, 46. Coordinate transformer 64 also stores the data indicating the pose of the working end of the surgical instrument relative to the instrument tracker 48.

During the procedure, the coordinate transformer 64 receives the data indicating the relative poses of the trackers 44, 46, 48 to the localizer 34. Based on these data and the previously loaded data, the coordinate transformer 64 generates data indicating the relative position and orientation of the coordinate system EAPP, and the bone coordinate systems, FBONE and TBONE to the localizer coordinate system LCLZ.

As a result, coordinate transformer 64 generates data indicating the position and orientation of the working end of the surgical instrument 22 relative to the tissue (e.g., bone) against which the instrument working end is applied. Image signals representative of these data are forwarded to displays 28, 29 enabling the surgeon and staff to view this information. In certain examples, other signals representative of these data can be forwarded to the manipulator controller 54 to guide the manipulator 56 and corresponding movement of the surgical instrument 22.

In a similar manner, other trackers may be coupled to any other suitable object to be tracked within the operating room, and each object and associated tracker may be registered to the localizer coordinate system LCLZ as described above.

An improved tracker array, and improved method of registration, or calibration, provide for improved tracking accuracy and stability and is less invasive to tissue and bone. In accordance with the present disclosure, first and second bone pins are affixed to a patient's anatomy, a plurality of fiducial markers are secured to the first and second bone pins or a combination of the first and second bone pins, a custom tracking arrangement of fiducials is defined within the navigation computer 26 incorporating the plurality of fiducial markers secured to the first and second bone pins and stored as a tracking array. The tracking array may have its own tracker coordinate system, or it may be a combination of the coordinate systems of fiducial markers supported by bone pins, plates or screws.

FIGS. 1-3 depict an improved tracker array comprising the trackers 44 and 46. Each of tracker 44 and 46 includes a tracker support which can be affixed to the object. Each of tracker 44 and 46 includes one or more fiducials or markers mounted on the tracker support. As described above, and in alternative examples below, the tracker support may comprise a bone pin, screw, plate or other suitable supporting structure mountable to an object to be tracked. In the tracker 44 and 46 example illustrated in FIGS. 1-3, the tracker support comprises a single bone pin affixed to the patient's tibia which extends integrally into a planar surface at the distal end. As described above, and in alternative examples below, the fiducials or markers may be include active LED markers, or passive reflective markers. In the tracker 44 and 46 example illustrated in FIGS. 1-3, the markers comprise adhesive reflectors 50 affixed to the tracker supports. In alternative examples, the markers may be pre-positioned on the tracker support, for example as laser-etched markings, inked markings, or adhered markings.

In a registration workflow for registering a patient's tibia, the trackers 44, 46 may include tracker supports that are pre-marked with an arrangement recognizable by the navigation computer, either through dimensional distribution or placement of the markers, color, size, shape or other designating characteristic. The navigation computer, storing information correlating to the patient's anatomy and to the patterns of markers on the trackers 44, 46, may automatically register the trackers 44, 46 to the anatomy (tibia T) for tracking during the procedure.

In alternative examples, where the trackers 44, 46 are not pre-marked and the navigation computer 26 not being provided pre-operative imaging of the patient's anatomy, during a registration workflow, the operator may be instructed to register, for example, the patient's tibia. In one example workflow, the operator would be instructed to attach a first and second tracker support to the object to be tracked, in this case—the patient's tibia T. Not being pre-marked, the operator would then be instructed to secure a plurality of markers 50 to the first and second tracker supports. The navigation computer 26, displaying images of the surgical space, may prompt the operator to define the marker arrangement forming the tracker by designating the markers securing to the tracker supports shown within the displayed images.

At this step, the navigation computer may evaluate the defined marker arrangement to ensure that the tracker is sufficiently unique to be differentiated from other trackers that may be registered within the navigation computer 26. If potential conflict is determined, the navigation computer 26 may prompt the user to further differentiate the tracker, by doing one or more of adding or removing markers 50 from the tracker supports 44, 46, modifying the placement of one or more markers on the tracker supports 44, 46, or adding an additional tracker support with yet more markers.

Continuing with the example workflow described, once the navigation computer accepts the defined marker arrangement forming the tracker, the tracker is registered to the object, in this example, the patient's tibia, T. Where the navigation computer 26 is not provided with pre-operative models or other geometry corresponding with the object to be tracked, the operator may provide input to designate the object based on imaging, perioperative scans, or other intraoperative tools. In one example, the navigation computer may prompt the operator to select the object to be tracked based on stereoscopic imaging of the patient's anatomy. The navigation computer 26 may further utilize morphed atlas models of the relevant anatomy to register the defined marker arrangement to the patient's anatomy. Once registered, the navigation computer may track the object based on the detected movement of the marker arrangements.

During tracking, the navigation computer 26 may be configured to monitor the tracking quality to ensure accurate and precise tracking is maintained. In one example, the navigation computer 26 may be configured to monitor and detect whether any marker in the defined marker arrangement deviates from the expected position relative to the other markers in the arrangement. If such a change is detected, it may indicate that one of the tracker supports may have come loose from the anatomy or be bent or otherwise displaced during the operation. The navigation computer 26 may generate a visible, or audible alarm to alert the operator that the tracking may have been compromised and that the object may need to be re-registered in the system. Upon detecting an error with the defined marker arrangement, the navigation computer 26 may be further configured to communicate an interrupt to the manipulator controller 54 to cause the robotic manipulator to stop its motion or to retreat to a safe position at a distance from the patient's anatomy, other tools, or operators in the surgical environment.

Figure 4B:
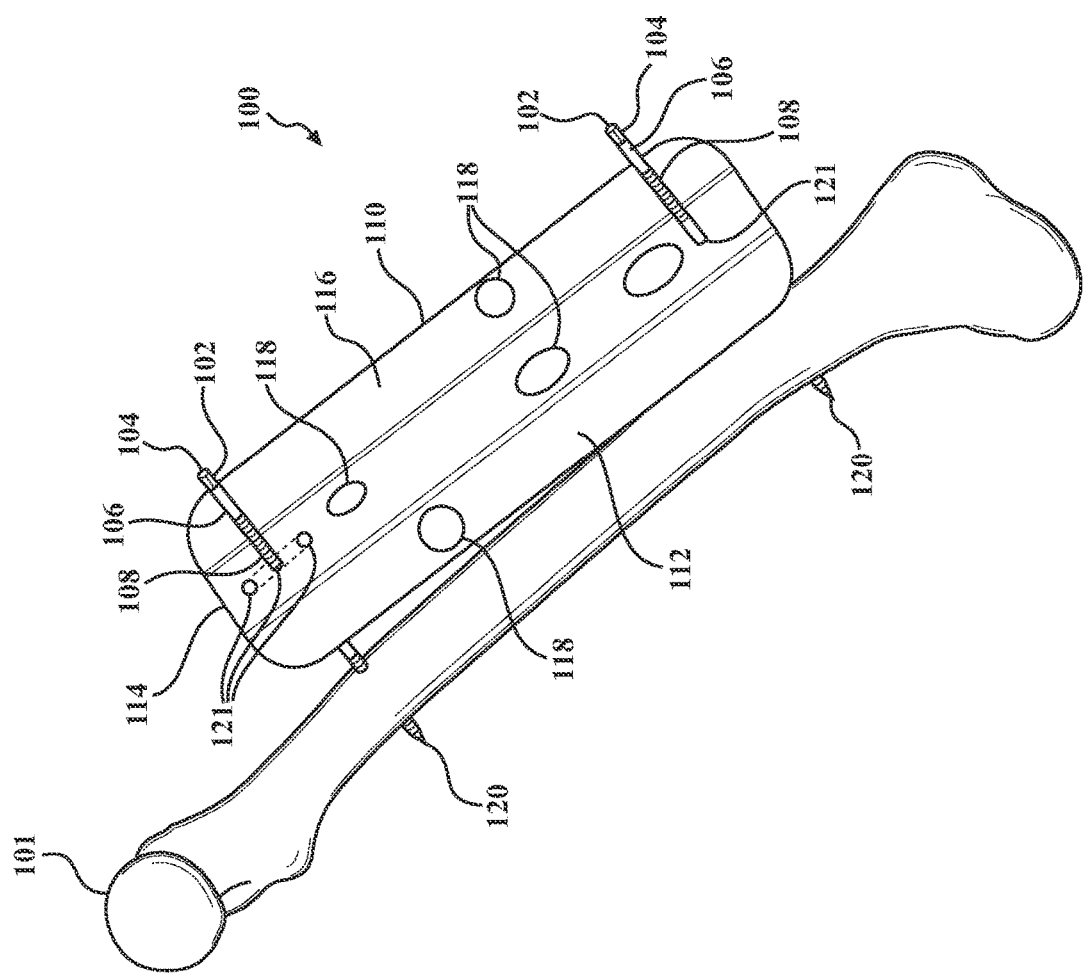
FIG. 4B is a first form of a tracker affixed to a bone, shown at a second angle.
Figure 4A:
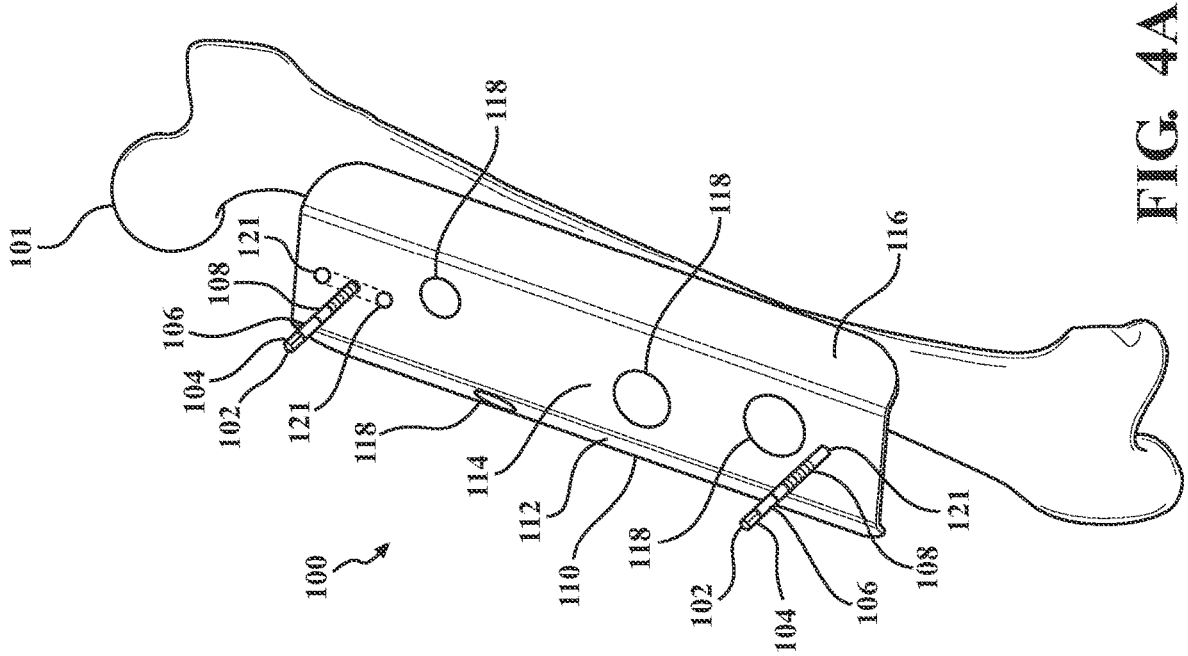
FIG. 4A is a first form of a tracker affixed to a bone, shown at a first angle.

An improved tracker 100 is shown in another example in FIGS. 4A and 4B to address and eliminate shortcomings associated with conventional surgical trackers. Tracker 100 is shown from two angles affixed to bone 101. Although illustrated as a femur, bone 101 could be any suitable bone or other tissue. The tracker 100 is affixed with two bone pins 102 disposed at opposite ends of bone 101. The bone pins 102 are adapted to support the tracker 100 in a rigid relationship with the patient's anatomy.

The bone pin 102 includes a feature 104 to allow the bone pin 102 to interface with a tool for inserting bone pin 102 as a drive feature. One example of feature 104 includes a plurality of flat surfaces of a predefined dimension to allow a tool to grasp the bone pin 102. Another example of feature 104 may include a spline, knurling, hex socket or other geometry configured to aid the transmission of torsional force from the tool to the bone pin 102. In some alternatives, the bone pin 102 excludes a drive feature, for example as a smooth cylinder. In such cases, a driver may clamp onto an accessible surface of the pin.

The bone pin 102 includes an elongated shaft 106 extending from the feature 104. Disposed along the length of the shaft 106 is a mounting interface 108. The mounting interface 108 may include a section of the shaft 106 that is threaded, conical or stepped, that is, a length of the shaft 106 may be of non-constant diameter. The mounting interface 108 provides a support point to secure plate 110 to the bone pins 102. The mounting interface may be structured so as to allow the plate 110 to be secured at a variable height relative to the bone pin 102. For example, where mounting interface 108 includes a threaded length of shaft 106, the height of the plate may be secured along the length of shaft 106 by rotating a nut (not shown) with complimentary threads. Similarly, separate nuts could be threaded on the shaft 106 on opposed sides of the plate 110 and tightened toward each other to secure the plate in position on the shaft 106. In further alternatives, tape, glue, curable or self-curing bonding materials can be used to secure the plate.

The plate 110 is supported at its respective ends by the bone pins 102 affixed in bone 101. In the form shown, plate 110 includes multiple surface portions 112, 114, 116 angled with respect to each other. The surface portions 112, 114, 116, may advantageously be positioned so that the visibility of the surfaces are maintained to the localizer even as the patient's anatomy is moved through multiple positions. In one alternative example, the plate can be formed or re-formed during the procedure. The plate may be provided with bendable portions that can be selectively adjusted to optimize the visibility of plate surfaces to the localizer. The placement and adjustment would occur prior to the registration of the object and tracker within the navigation computer 26. Once tracking was initiated, following registration, the static configuration of the tracker components relative to other components making up the tracker, and the static relationship between the tracker and the object, is generally used by the navigation computer to ensure that accurate and precise tracking is maintained. The navigation computer 26 may be configured to periodically check and confirm the relative relationship between individual markers comprising the tracker, or a portion or the tracker relative to other portions, to ensure that tracking has not been impeded. Upon detecting a change in the tracker configuration, either internally or relative to the tracked object, the navigation computer 26 may generate a warning alarm, such as an audible or visible alert. Additionally, the navigation computer 26 may interrupt the manipulator controller 54, directing it to cease operation of the manipulator arm 58 or withdraw the instrument 22 to a safe position.

Affixed to one or more of the surface portions 112, 114, 116 of plate 110 are markers 118. The markers 118 are the fiducial points of the tracker that allow the localizer to locate and track the object, in this case bone 101, to which the tracker 100 is affixed. The markers 118 may be one or more of adhesive-backed markers, laser-etched marks, inked or printed marks, or other suitable marking detectable by the localizer 34. Although depicted as circles, alternative markers 118 may include other shapes and figures. In particular, the markers 118 may be particularly configured to provide human-readable or machine-readable information. In one example, an "F" form may be provided to designate a tracker attached to a patient's Femur, and a "T" from may designate attachment to a patient's Tibia. Similarly, marker 118 may include one or more bar code, QR code, color pattern or other information encoding marking recognizable to the navigation computer 26.

In one example, marking 118 is an adhesive-backed IR-reflective sticker. In this example, the localizer 34 includes IR-sensitive optical sensors 40 and one or more IR-emitting LEDs provided on the camera unit 36. At the beginning of a surgical operation, two bone pins 102, as first and second tracker supports, are affixed to bone 101. In this example, the bone pins 102 are inserted into the bone using a powered drill having a Jacobs chuck to rotate the bone pins 102 so that they screw into the bone 101. The bone pins 102 include a self-drilling end feature 120 and are threaded along their length to secure to the bone 101.

In the illustrated example, the bone pins 102 are shown at opposite ends of a femur bone 101. In other applications, bone 101 may be any other suitable bone. For example, bone 101 may be a tibia. From patient to patient, the length of the bone will vary and therefore the distance between the bone pins 102 will likewise vary. Therefore, the plate 110 must accommodate different separation distances.

The plate 110 may be provided with multiple apertures 121 so that appropriate separation distance between the bone pins 102 may be selected for the bone to be tracked. The apertures 121 may be formed in the plate 121, for example, by drilling through the plate. An operator may use at least one aperture 121 formed in the plate 110 prior to beginning an operation, and may form a second aperture during the procedure by selecting an appropriate location on the plate 110 in relation to the patient's anatomy for a second secure point of mounting. To accommodate a wider range of distances between bone pins 102, plate 110 may include a circular aperture 121 at one end and include an aperture formed as an elongated slot (indicated in the FIGS. 4A, 4B in dashed lines). Multiple plate 110 options may be available having different lengths so that a suitable plate 110 can be selected for the particular application.

The plate 110 mounts to the bone pins 102 to be supported thereon at a height above the skin of the patient. The height at which the plate 110 mounts to the bone pins 102 may, in some cases, be directly adjacent and in contact with the patient's skin. The incision needed for the tracker 100 may be less invasive than needed for conventional trackers. Conventional trackers may require multiple bone pins to be placed in close proximity so that a single, large incision is needed to encompass both pins. The tracker 100, having bone pins 102 disposed at opposite ends of the bone allows separate, smaller incisions that may provide the patient faster recovery.

The plate 110 may be pre-marked, or markers 118 may be placed on the plate 110 after it has been mounted to the bone pins 102. In applications where the plate is pre-marked, for example with laser-etched markings, the placement of the markers 118 on the plate 110 may be in a pre-defined arrangement. The pre-defined arrangement of markers 118 may correspond to one of a known library of pre-defined arrangements corresponding to identifiable objects. For example, in one application the particular arrangement of laser-etched markers may be stored in the navigation computer 26 to correspond to and identify the object as a femur. In such an application, alternative plates may be pre-marked with marker arrangements to identify one or more bones to be tracked as part of the surgical operation. The operator would select the appropriate plate 110 to mount to the proper bone so that the navigation computer 26 associates the tracker 100 with the object based on the recognized pattern of markers 118 on the tracker 100.

In applications where the plate 110 is not pre-marked, the operator would apply markers 118, such as adhesive-backed stickers, to create an arrangement to be identified to the navigation computer 26 and which thereafter can be tracked by the navigation system 20. Once applied to plate 110, the operator may identify to the navigation system 20 the markers comprising the tracker 100 by providing input and/or making selections through touch screen 30. For example, in an operation where multiple bones are being tracked, the operator may need to differentiate the markers 118 applied to a plate 110 affixed to a femur from a plate affixed to a tibia. The tracker 100 in this example allows the in situ definition of a marker arrangement to track and identify a particular object.

Figure 5C:
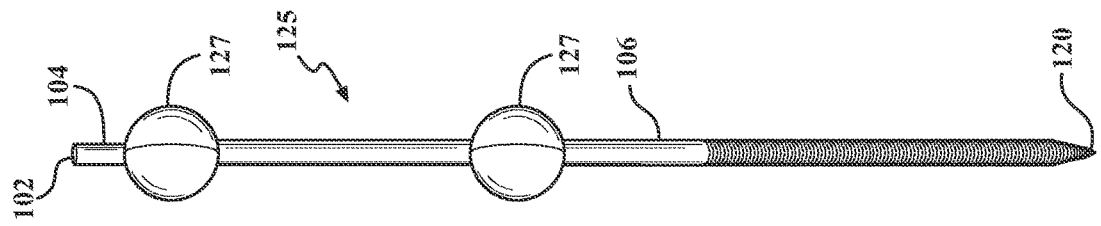
FIG. 5C is a second form of a tracker in a third illustrated example
Figure 5B:
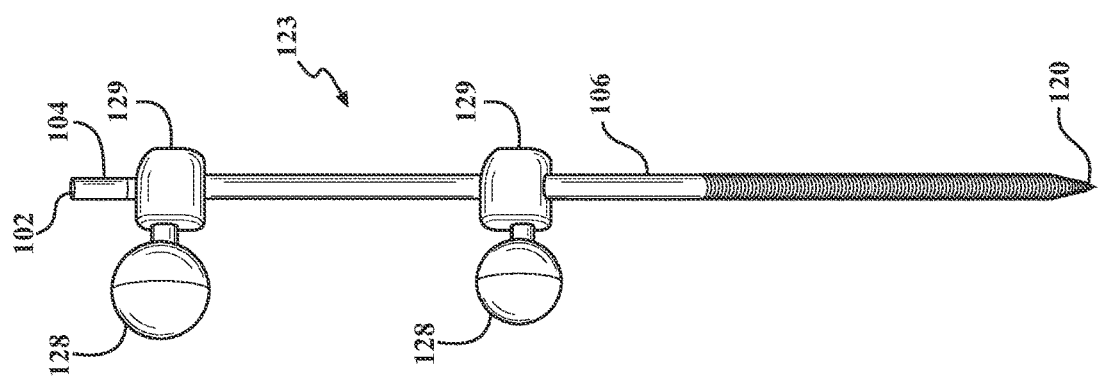
FIG. 5B is a second form of a tracker in a second illustrated example.
Figure 5A:
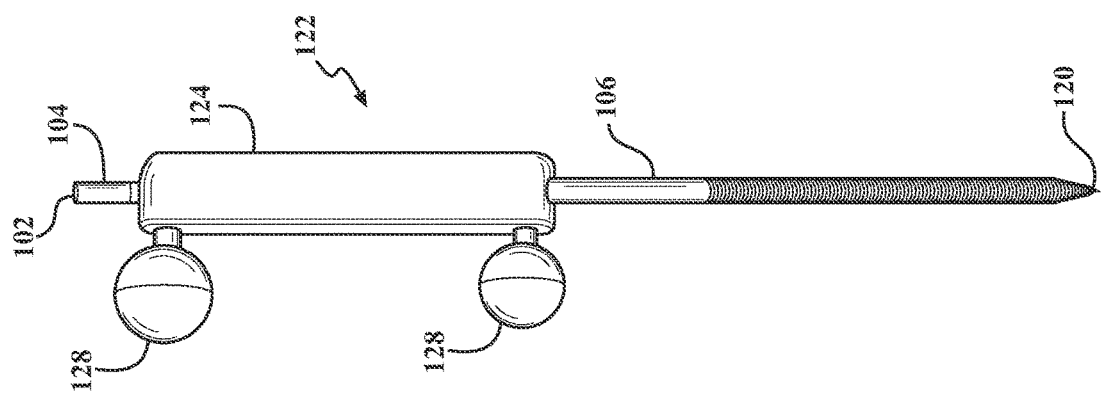
FIG. 5A is a second form of a tracker in a first illustrated example.

An alternative form of a tracker 122 according to the present disclosure is illustrated in FIG. 5A. The tracker 122 includes a bone pin 102 and sleeve 124. The bone pin 102 is affixed to the bone or object to be tracked as described above. After the bone pin 102 is affixed, sleeve 124 is mounted to the bone pin 102. The sleeve 124, similar to plate 110, is supported on the bone pin 102 at a height along the bone pin 102 a distance from the patient's anatomy. The sleeve 124 includes a complementary feature (not shown) to interact with mounting interface 108 and allow the sleeve 124 to be secured to the bone pin 102, and may include, for example, a set screw.

Supported on the sleeve 124 are one or more fiducial markers 128. In one example, the markers 128 are reflector balls provided with a material or coating adapted to reflect infrared light. In another example, the markers 128 are LEDs that emit light in the near infrared wavelength. In this way, the markers 128 provide signals 53 to the optical sensors 40 of the localizer 34. The sleeve 124 and markers 128 may have a known geometry that can be stored in the navigation computer 26. Specifically, the markers 128 may be spaced apart along the sleeve 124 by a defined distance. Additionally, the markers 128 may be a defined radial distance from a center point or axis of the bone pin 102. The sleeve 124 may be rotatable about the bone pin 102 to be positioned on the bone pin 102 for optimal visibility to the localizer 34. The sleeve 124 may further be securable to the bone pin 102 once positioned so that further rotation is restricted. For example, one or more set screws may be used to secure the sleeve at a desired position and/or orientation along the bone pin 102. In alternative examples, tape, glue, curable or self-curing bonding materials can be used to secure the sleeve 124 to the bone pin 102. In the example shown, the sleeve 124 is generally cylindrical and capable of rotation about the bone pin 102 and sliding relative to the bone pin 102 prior to being secured in place to maintain direct visual line-of-sight to the localizer 34.

A further alternative form of a tracker 123 is illustrated in FIG. 5B. The tracker 125 includes a similar bone pin 102 as in the prior example. In place of the sleeve 124 controlling a fixed distance between the markers 128, the markers 128 in FIG. 5B are separately supported on rings 129. The rings 129 may include complementary features to interact with a mounting interface 108 on the bone pin 102 to allow the rings 129 to be secured to the bone pin 102. In alternative examples, tape, glue, curable or self-curing bonding materials can be used to secure the rings 129 to the bone pin 102.

Similarly as with the sleeve 124 described above, the rings 129 can be rotated and slid relative to the bone pin 102 prior to being secured in place. Each ring 129 allows the respective marker 128 to be selectively positioned on the bone pin. This allows the multiple markers 128 along the bone pin 102 to be at different rotational positions. That is, the markers 128 may not be aligned along one side of the bone 102, unlike the configuration illustrated in FIG. 5B. In a further alternative, the ring 129 may be configured to support the marker 128 at different distances away from the bone pin 102. Once the bone pin is inserted, the markers 128 may be positioned in the best orientation to be visible to the localizer 34.

Another alternative tracker 125 is illustrated in FIG. 5C. The tracker 125 likewise includes a bone pin 102. In this example, the marker 127 is a spherical marker that can slide over the bone pins 102. The spherical markers 127 offer improved visibility over the markers 128 mounted offset from the bone pin 102. The markers 127 are visible from any side of the bone pin 102, and is not blocked by the bone pin 102 in the view of the localizer 34.

Figure 6:
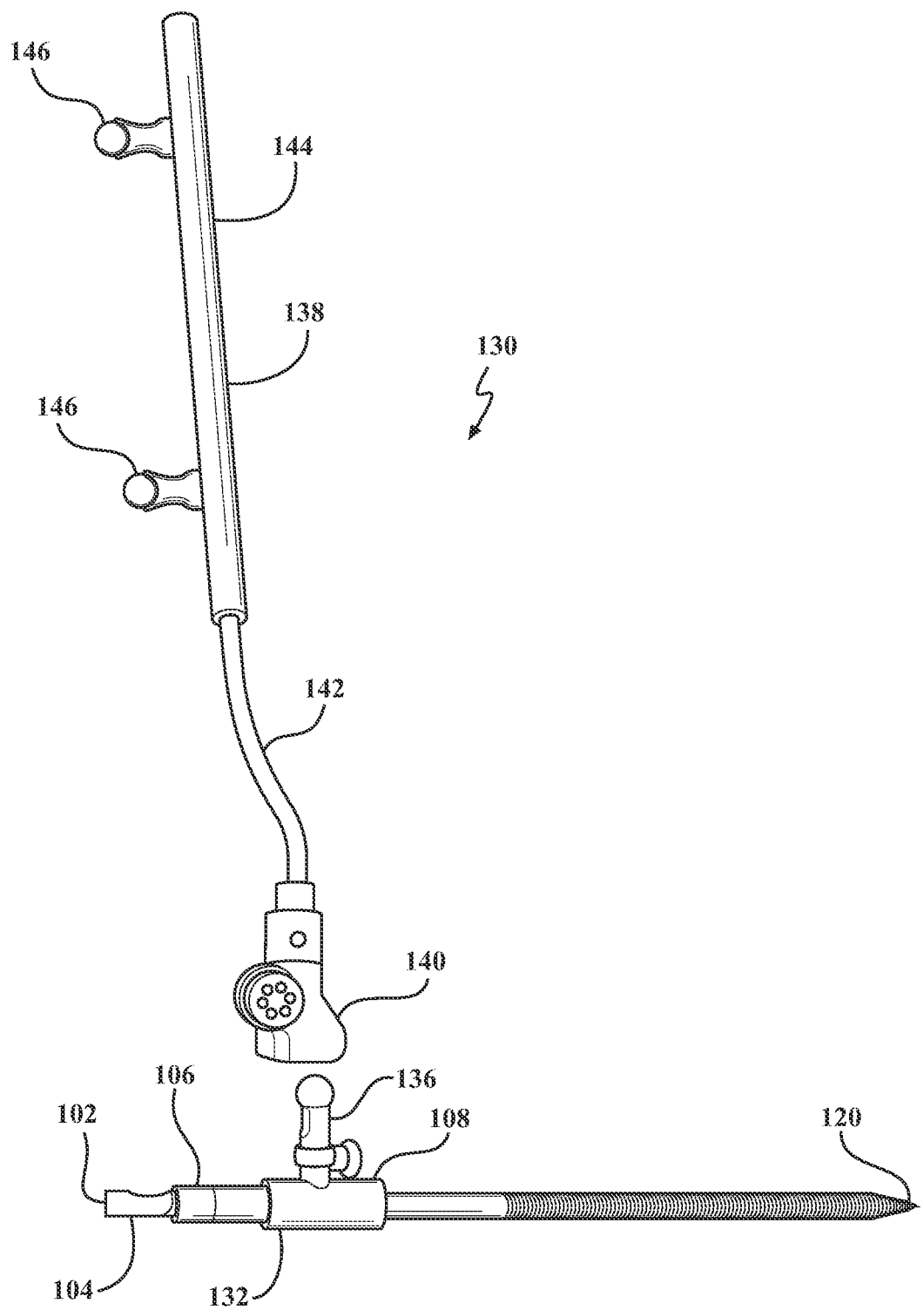
FIG. 6 is a third form of a tracker.

A related alternative form of a tracker 130 according to the present disclosure is illustrated in FIG. 6. The tracker 130 likewise includes bone pin 102, but the fiducial support 138 is offset from the bone pin 102 in this form. Rather, supported on bone pin 102, collar 132 is disposed along the length of the shaft 106 and is secured to the mounting interface 108. The collar 132 further supports a post 136 extending from the collar 132. A clamp 140 secures to the post 136 and allows the support 138 to be adjusted and positioned prior to being rigidly affixed in place. Extending from the clamp 140, stem 142 allows the fiducial markers 146 to be further offset from the bone pin 102. The clamp 140 and post 136 may be like those shown in U.S. Patent Application Publication No. 2017/0340395 to Perez, entitled, "Navigation Tracker With Kinematic Connector Assembly," hereby incorporated herein by reference. In alternative examples, markers 146 may be arranged similarly as shown in FIGS. 5A-5C. For example, stem 142 may extend to provide sufficient mounting space for markers 146 to be independently mounted on rings (not shown, but see FIG. 5B); or as spherical markers (see FIG. 5C).

Stem 142 may be formed of a bendable and/or malleable material that allows the operator to impart a plastic deformation to the stem prior to the operation to precisely arrange the markers in the desired position. The stem 142 may be formed of a strain hardening material that resists subsequent deformation after an initial adjustment is made. Example materials include titanium, its alloys, copper, brass, and spring steel. The markers 146 are supported on shaft 144, which rigidly retains the markers 146 in a static positional relationship relative to each other.

Similar to the sleeve 124 and markers 128, the shaft 144 supports the markers 146 in a known geometry that can be stored in the navigation computer 26. Specifically, the markers 146 may be spaced apart along the shaft 144 by a defined distance. The markers 146 may be a defined radial distance from a center point or axis of the shaft 144. The shaft 144 may be rotatable about the stem 142 to be positioned for optimal visibility to the localizer 34. This rotation could be provided by virtue of the malleability of the stem 142, if the shaft 144 and stem 142 are fixed together, or the shaft 144 may be a separate component from the stem 142. The shaft 144 may further be securable once positioned so that further rotation is restricted, such as by set screws as described above.

Figure 7:
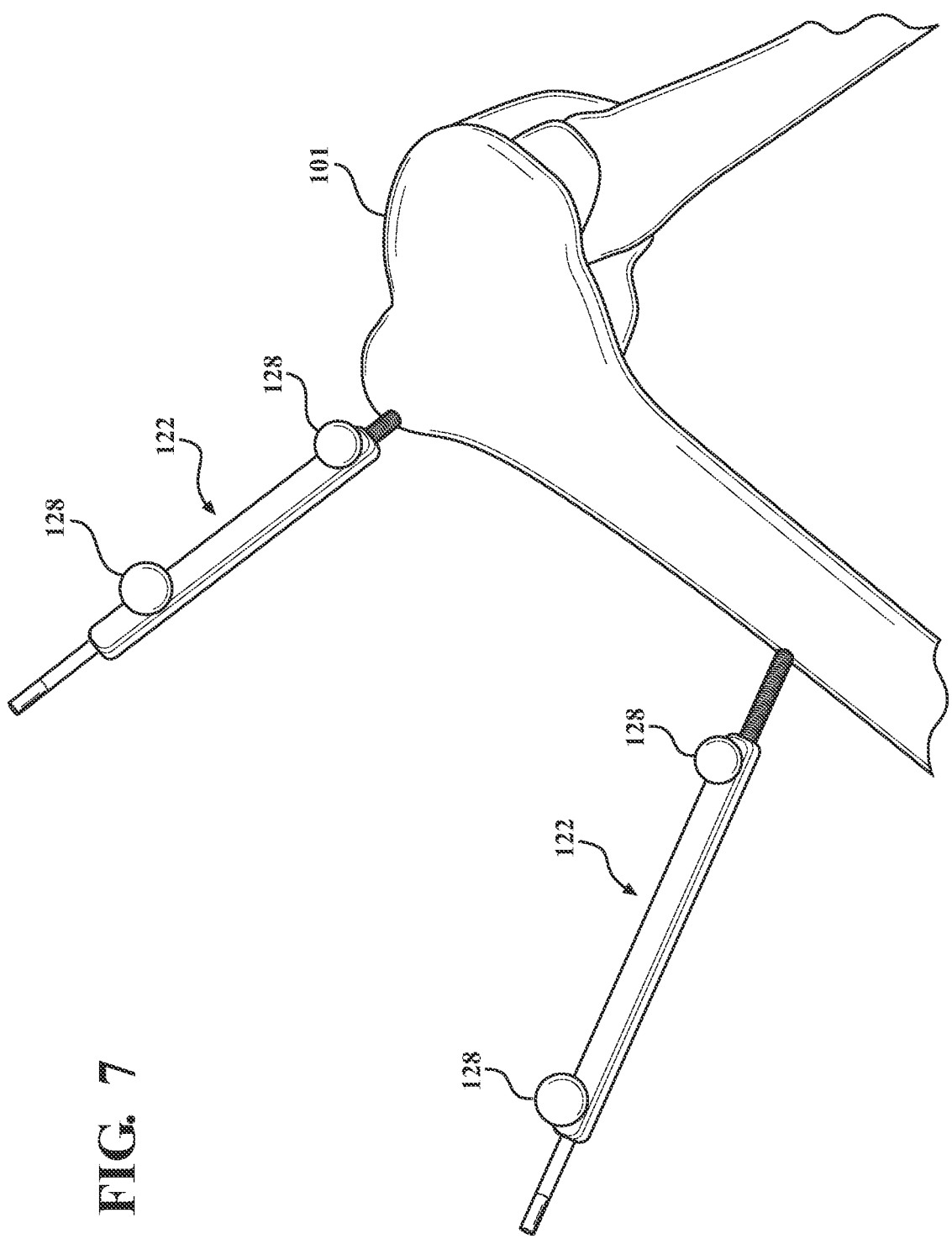
FIG. 7 shows trackers according to the second form affixed to a bone.
Figure 8:
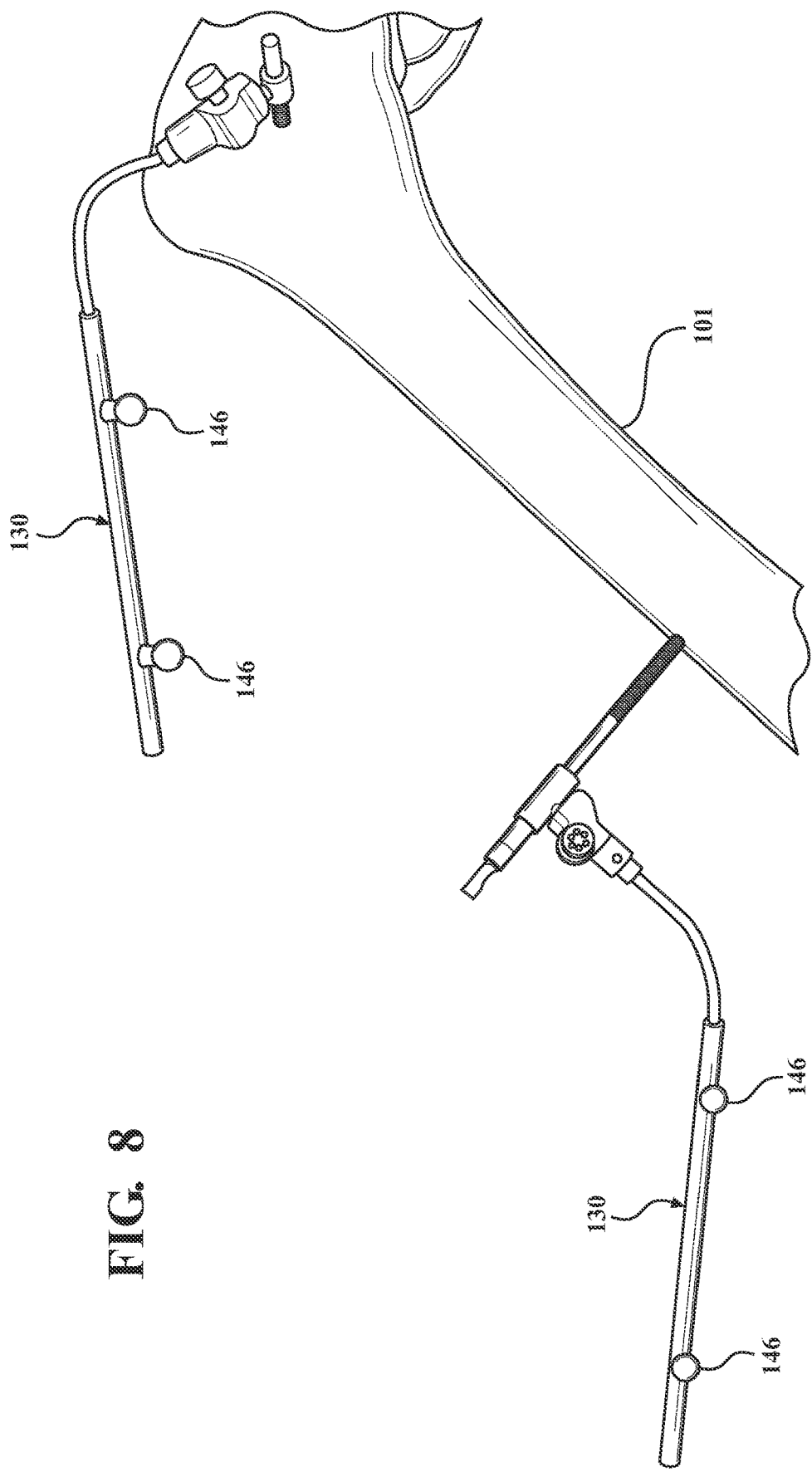
FIG. 8 shows trackers according to the third form affixed to a bone.

FIGS. 7 and 8 illustrate applications of the trackers 122 and trackers 130, respectively. In both cases, two bone pins 122, 130 are affixed to the bone 101. The bone pins 102 of trackers 122 and trackers 130 can be individually placed into the bone spaced apart from each other. In this way, the trackers 122 and trackers 130 can provide a greater distance between markers than with a conventional frame-based tracker.

During registration, the localizer images the target space including the object to be tracked, for example, a patient's anatomy, and the trackers affixed to the object. The trackers 122, 130 affixed to the patient's anatomy may be detected by the navigation computer 26 or may be selected by the user to be designated as a single tracking array. Once designated, the relative positions of the four markers, distributed between the two trackers 122, 130, is stored in the navigation computer 26 in a defined relationship. The rigidity of the bone, combined with the rigid affixation of the trackers 122, 130 to the bone, and the defined geometric relationship of the two markers on each pin 122, 130 provides the navigation computer 26 with information to perform a rigid transformation of the coordinate systems of the trackers to the coordinate system of the localizer. In this way, the navigation computer can track the movement of the object in three dimensions by tracking the movement of the markers.

A further improvement is realized in the use of the trackers 122, 130 by eliminating the need for a checkpoint screw. Owing to the separate, rigid attachment of the two trackers 122, 130 and the defined relationship between the two markers on the trackers 122, 130, each tracker 122, 130 can act as a continuous checkpoint for the other of the trackers commonly affixed. The navigation computer 26 can track the location of the trackers 122, 130 in order to track the location of the object and can track the location of the trackers 122, 130 relative to each other to ensure that the registration remains true.

To provide full tracking, the present disclosure described affixing multiple tracker supports to the object to be tracked, with each tracker support including multiple markers. A single tracker support, including a single marker, may be used to provide some level of partial tracking. Small objects, including those expected to be subject only to small displacements, may be registered with a single marker point to define a tracking relationship relative to other registered objects. In one example, a single tracking support is registered to a patient's patella in order to provide partial tracking relative to the patient's femur F, tibia T, or both.

Figure 9:
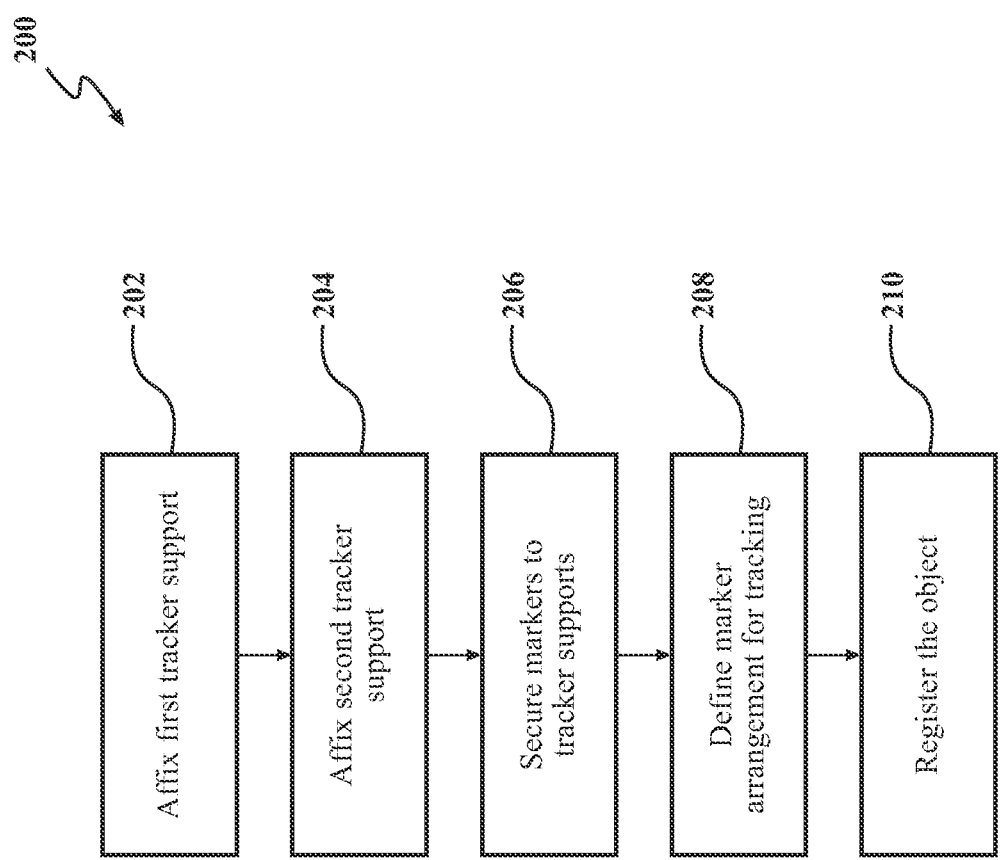
FIG. 9 is a flowchart illustrating the steps of a method for tracking.

Referring now to FIG. 9, a method 200 of tracking an object is provided. Prior to a surgical operation, the target site of a patient's anatomy is prepared for surgery. As part of the preparation, one or more trackers may be affixed to the patient's anatomy and registered to the navigation system 20. At step 202 of the method, a first tracker support is affixed, for example, to a patient's femur. The first tracker support includes bone pin 102, which may be affixed by first making a small incision in the patient's leg to expose the bone for the surgeon's access. Once the bone is exposed, the surgeon may employ a power drill or other suitable tool to screw the bone pin 102 into the bone. The bone pin 102 is provided with a feature 104 to engage with the drill, and an end feature 120 to facilitate screwing into the bone. At step 204, a second tracker support is affixed to the object to be tracked at a location spaced apart from the first tracker support. The second tracker support includes a second bone pin 102 and is affixed in the same manner as the first.

At step 206, a plurality of fiducial markers are secured to the first tracker support and the second tracker support. In one example, this step may be performed by supporting a plate 110 at each end on the first and second tracker supports. The plate 110 may be provided with markers 118 formed thereon or which are applied once the plate 110 has been supported on the first and second tracker supports, such as through the application of adhesive-backed IR-reflective stickers. In a second example, the step of securing the fiducial markers to the tracker supports may be performed by attaching a sleeve 124 onto each of the first and second tracker supports. The sleeve initially may be rotationally adjustable on the tracker support and, once positioned, secured into place to resist further rotation. In a further alternative example, this step of securing the fiducial markers to the tracker supports may be performed by sliding a collar 132 including a post 136 onto each of the tracker supports and thereafter clamping a fiducial support 138 onto the post by a clamp 140. The fiducial support may provide for additional positional adjustments before being finally secured in place.

At step 208, a marker arrangement is defined in the navigation computer to be associated with object to be tracked. The markers defining the arrangement are supported by tracker supports spaced apart from each other on the object to be tracked. In one example, the tracker supports are bone pins disposed at opposite portions of a bone and support an elongated plate 110 containing the markers 118. The navigation computer 26 may recognize the pattern of markers on the plate 110, if, for example, the plate 110 is pre-marked with the markers 118 in a pre-defined arrangement. The navigation computer 26 may store a library of known marker arrangements and correlate the detected pattern to one of the known arrangements. Alternatively, the operator may provide an input, for example, through touch-screen 30, to select from among the library of known marker arrangements, which the navigation computer 26 will thereafter associate with the detected pattern of markers on the plate.

Defining the marker arrangement for tracking, at step 208, in another example, does not require any pre-defined arrangement of markers to be stored in navigation computer 26. Rather, the operator may be creating the arrangement in the course of performing the actions of steps 202-206. That is, the operator may be applying the markers 118 to the plate 110 in addition to securing the plate 110 to the tracker supports. Likewise, assembling the trackers 122 and trackers 130 creates a unique arrangement of markers 128, 146 in the relationship between the first and second tracker supports. Even though the relationship from one marker 128, 146 to the other on each tracker 122, 130 is predefined according to the manufactured geometry, the relationship between one tracker 122, 130 to the other tracker 122, 130 is not established until the tracker supports, have been affixed.

In an example application, where the navigation computer 26 does not have a pre-defined arrangement of markers stored from which to reference, the operator may be presented with a prompt by the navigation computer to selectively designate which markers will define the arrangement for tracking the object. The operator may perform this designation, in one example application, by using the navigation pointer P to touch off each tracker 122, 130 to designate its inclusion to the navigation computer 26, which is then stored for subsequent use during tracking. In another example application, the navigation computer 26 will present the operator with the detected marker points, for example, displayed on screen 29, and allow the operator to select which of the detected marker points will define the arrangement for tracking. This may be a similar action where the operator has applied markers to the plate 110.

At step 210, the defined marker arrangement is registered to the object within the navigation computer 26 to allow the object to be tracked within the virtual environment according to the movements of the markers comprising the defined arrangement. In a process similar to the conventional registration, preoperative images of the object to be tracked are used to generate a virtual 3D representation or model of the object. Using the pointer P or other registration process, the defined marker arrangement of step 208 is associated with the object model in the virtual environment of the navigation computer 26. Once registered, the navigation system 20 can provide precise information about the position and orientation of the object by tracking the movement of the tracker.

Although described in separate examples, elements from the many examples may be combined, swapped, modified or employed based on the description of other examples. For example, the bone pin 102 shown in FIGS. 4A and 4B, supporting plate 110, may further support a spherical reflector ball-type marker as described in connection with the example illustrated in FIG. 5C. More generally, a single tracker support may include multiple types of fiducials or markers. A tracker, such as 44 or 46 as in FIGS. 1-3, may be pre-marked with one or more markers, such as a laser-etched pattern that is recognizable by the navigation computer 26, and is thereafter further marked with additional, reflective stickers to differentiate and define unique marker arrangements for each object to be tracked. Moreover, the tracker may support both active and passive trackers according to the needs or preferences of the operator.

Registration Recovery

As described above, the navigation system 20 is configured to monitor and detect whether any marker in the defined marker arrangement deviates from the determined position relative to the other markers in the arrangement. Such changes may occur, for example, when one of the tracker supports becomes loose from the anatomy, is bent, or is otherwise displaced with respect to the anatomy. In such instances, the registration may be lost.

However, the versatility and functionality of the tracker configurations described above advantageously provide for the ability to easily recover lost registration. As used herein, registration recovery is the process by which markers of a displaced tracker can be returned to the position and/or orientation of the original geometry of the markers that existed at the time of registration, thereby restoring the original registration without repeating the registration process. This recovery feature is enabled by the dynamic configuration of separately affixed and adjustable trackers, which also serve as a continuous checkpoint for each other. This registration recovery feature advantageously saves a significant amount of time in the operating room because a complete registration process need not be repeated when registration is lost.

The techniques herein provide for the navigation system 20 to identify conditions wherein at least tracker or marker of the arrangement (defined according to any of the components or techniques above) is displaced relative to an original registered geometry of the arrangement. The navigation system 20 can then take actions to either automatically correct this condition or guide a user to address the condition.

The registration recovery process can begin, for example, when the navigation system 20 automatically detects tracker displacement and loss of registration. If registration is lost, the navigation system 20 can automatically notify the operator that registration has been compromised.

Once registration is lost, there are different scenarios by which registration recovery can be initiated and performed. In one example, the navigation system 20 can further detect whether the error condition that occurred (e.g., the tracker displacement) is a candidate for registration recovery. For example, the navigation system 20 can evaluate the magnitude and/or direction of the displacement with respect to an acceptable threshold or tolerance. The threshold may be predetermined based on data from the original registration, possible range of motion of the tracker(s), the relationship between the separately affixed trackers to each other or to the bone, or any combination thereof. If the displacement satisfies the displacement threshold, then the navigation system 20 can determine that registration recovery may be possible. The navigation system 20 can also evaluate tracker movement over time, e.g., to determine whether the tracker is stable enough for registration recovery. For example, the navigation system 20 can determine that the tracker is still stably affixed to the bone, but the marker is in a different position. Alternatively, the navigation system 20 can determine that the tracker is too unstable for registration recovery (e.g., when the bone pin is too unstable), thereby requiring repeating of the full registration process. There may techniques other than those described herein by which the navigation system 20 can detect loss of registration and optionally, whether the tracker condition is a candidate for registration recovery. If registration recovery is possible, the navigation system 20 can automatically notify the operator that registration recovery can be performed.

In some instances, the operator is aware which bone pin, tracker, or marker(s) was displaced from its position and/or orientation that existed at the time of registration. For example, the user may have witnessed the displacement. In such instances, the navigation system 20 can instruct registration recovery steps in conjunction input based on the knowledge of operator. Alternatively or additionally, based on the operator's knowledge that the error condition is recoverable, the user may manually initiate the registration recovery process using input devices (e.g., display 30) of the navigation system 20. For example, the operator can input to the navigation system 20 which tracker was displaced thereby decreasing the time needed to identify the error condition and recover registration.

In either instance, once the registration recovery process is initiated, the navigation system 20 monitors the tracker pose during recovery and the operator can manipulate the bone pin, tracker or marker(s) until the navigation system 20 determines that the original geometry is restored.

Figure 10:
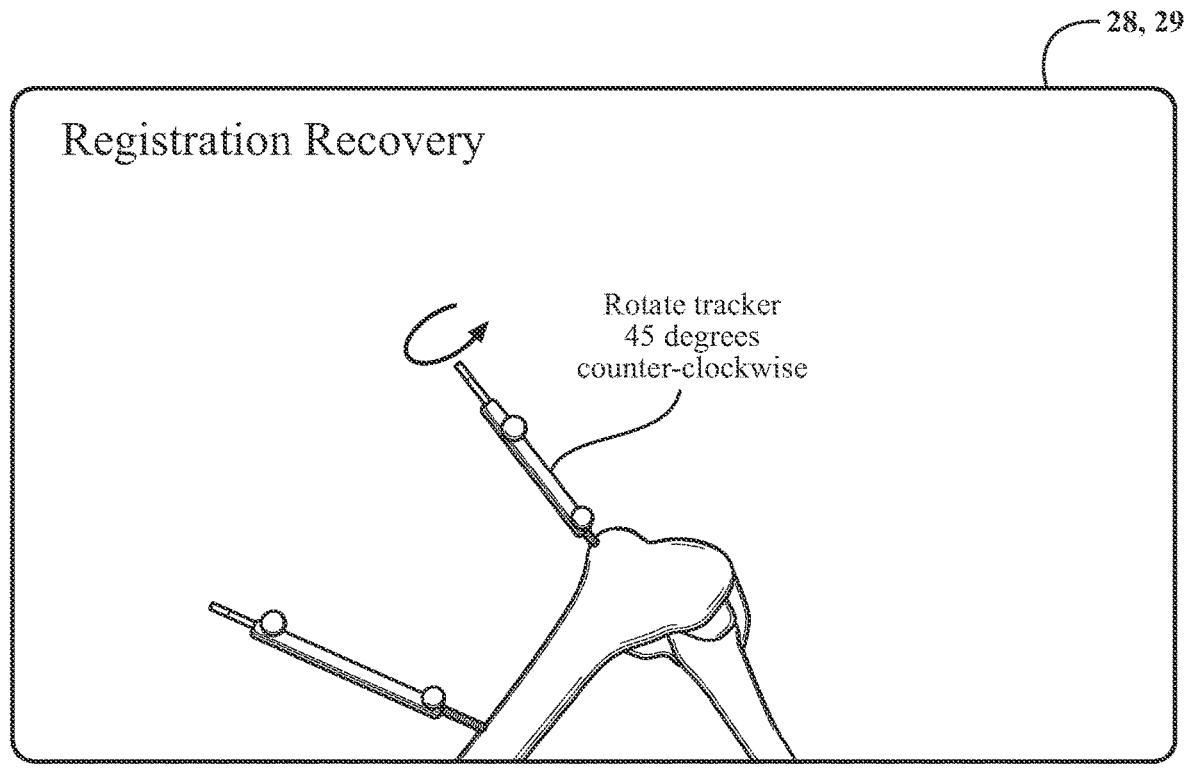
FIGS. 10 and 11 illustrate visual guidance or instructions generated by the navigation system to assist an operator in recovering registration using the trackers described herein.

Referring to FIG. 10, the error condition causing loss of registration may have occurred because movement occurring at a rotatable feature of the tracker. The rotatable feature can be the threaded connection, such as the connection between the threaded mounting interface 108 of the bone pine 122 to the bone. Additionally or alternatively, the rotatable feature can be the sleeve 124 of the tracker described above. The rotatable feature can be other features not described herein. The navigation system 20 can determine that a change in orientation of tracker about the axis of rotation is needed to recover registration and can instruct or guide the operator to rotate the feature (as shown) to its original position to recover registration. To facilitate this process, the navigation system 20 can provide information on the display(s) 28, 29 to assist the operator in recovering the position and/or orientation of the tracker or bone pin that existed at the time of registration. In FIG. 10, the tracker has the configuration of the tracker 122 shown in FIGS. 5A and 7. The navigation system 20 can show a camera-based or virtual representation of the tracker and bone to facilitate the correction. In this example, the navigation system 20 specifically instructs the operator to rotate the tracker in a certain direction and by a certain magnitude to reach the original geometry of the tracker configuration. The navigation system 20 monitors the behavior of the tracker during this correction and will notify the operator once registration is recovered. The guidance can include messages, videos, animations showing the exact correction needed, or the like. Other examples of guidance provided by the navigation system 20 are contemplated.

Figure 11:
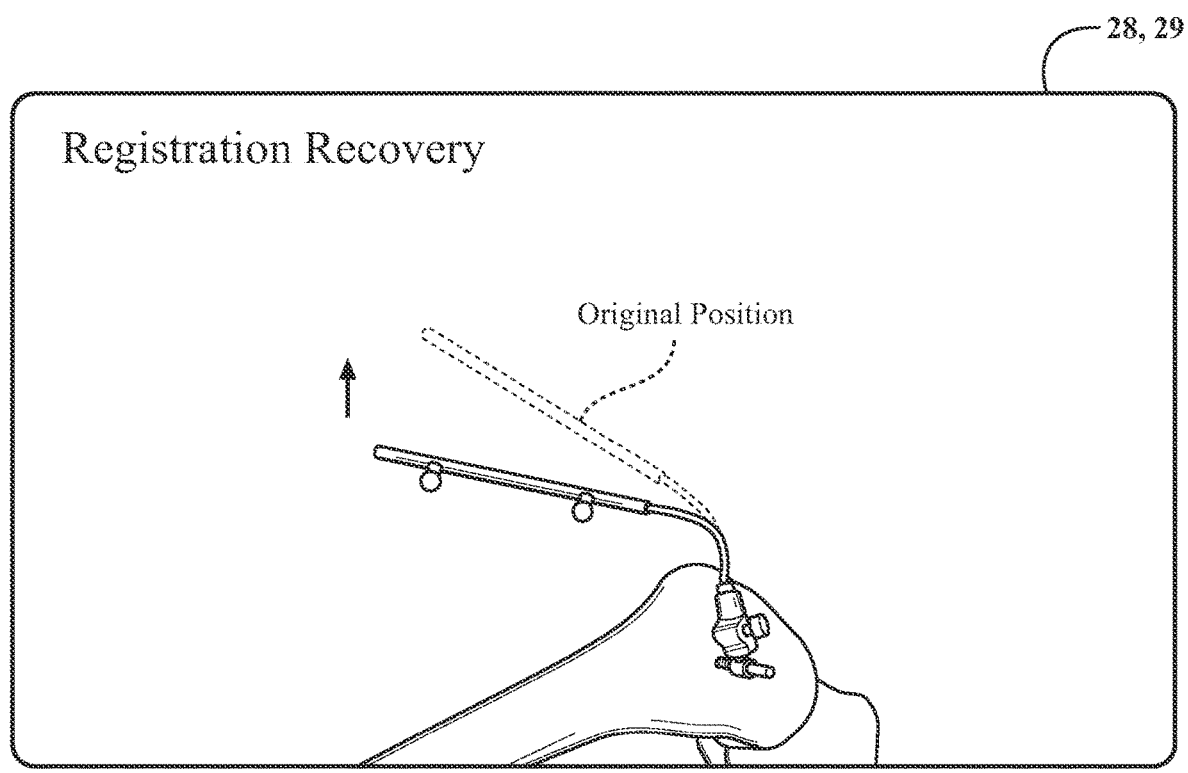

In another example, and referring to FIG. 11, the error condition causing loss of registration may have occurred because movement of a flexible part of the tracker. For instance, the flexible stem 142 of the tracker 130 of the example of FIG. 8 may have inadvertently moved from its original position. The navigation system 20 can determine that a flexing of the stem 142 is needed to move the tracker to its original position to recover registration. In this example, the navigation system 20 shows a virtual representation of the tracker in the original positon on the display(s) 28, 20. The operator can then flex the stem 124 while observing the real-time monitored movement of the stem 124 and tracker on the display 28, 29 until the tracker is properly positioned in the original position. This type of guidance may be useful where the correction is difficult to explain with specific instructions (as in FIG. 10). Once the tracker reaches the original position, the navigation system 20 can notify the operator of a successful recovery. In one example, the virtual representation of the tracker in the original positon may, for example, be highlighted to visually show the operator that the tracker position is properly restored. Other examples of such notifications may be through audible, haptic, textual and/or other visual techniques.

In other instances, the operator may not be aware that the bone pin, tracker or marker(s) was displaced from its position and/or orientation that existed at the time of registration. Again, the navigation system 20 can automatically notify the operator that registration has been lost. However, when the operator is unaware, he/she cannot provide input to the navigation system 20 about which tracker was displaced. If the navigation system 20 cannot automatically determine which tracker has been displaced, there may be additional techniques that the navigation system 20 can utilize to identify which tracker is displaced.

In one example, once registration is lost, the navigation system 20 can instruct the operator to use the navigation pointer P to digitize an anatomical landmark. The anatomical landmark can be one instructed by the navigation system 20 or one that the operator selects using his/her judgement. Since the pointer P is tracked, the selected landmark is registered by the navigation system 20. The navigation system 20 then computes a distance between the anatomical landmark and each marker (e.g., any of the markers 118, 127, 128 or 146) of the tracker setup. From these distances, and the original geometry of the tracker setup, the navigation system 20 can then identify which tracker is displaced from the original geometry. Registration recovery can then be performed for the identified tracker.

In a variation of the above example, the robotic manipulator 56 can be utilized to touch the anatomical landmark, instead of the navigation pointer P. More specifically, the robotic manipulator 56 can utilize the attached surgical instrument 22 or energy applicator EA to touch the anatomical landmark. The selected anatomical landmark can be registered in different ways. In one example, the navigation system 20 tracks the position of the instrument tracker 48 on the robot 56 and fuses this data with known relationship data between the instrument tracker 48 and the instrument 22 and known relationship data between the instrument 22 and a tool center point of the energy applicator EA. Additionally, or alternatively, the anatomical landmark can be determined based on the kinematic pose of the robotic manipulator 56 and the known relationship between the instrument 22 and the tool center point of the energy applicator EA. In either instance, the navigation system 20 can compute the distances between the selected anatomical landmark and the markers to determine which tracker is displaced from the original geometry, as described above. Registration recovery can then be performed for the identified tracker.

In another example, the pointer P can be utilized to digitize the bone pin at a region where a base of the bone pin contacts the bone. Once this point is registered by the navigation system 20, the navigation system 20 can compute a current distance between the digitized point and one or more markers of the tracker attached to the respective bone pin. These current distances can be compared with the original distances between the markers and the base of the bone pin that existed at the time of registration. If the navigation system 20 determines that the current and original distances are different, the navigation system 20 can determine that this tracker is the one that has experienced some displacement from the time of registration. The recovery process can then be carried out with respect to the identified tracker. On the other hand, if the navigation system 20 determines that the current and original distances are identical, the navigation system 20 can determine that this tracker has not experienced any displacement from the time of registration. Therefore, by process of elimination, the other tracker is identified as the one having experienced displacement, and the recovery process can then be carried out with respect to the other tracker.

Other examples to identify the error condition may be performed without the need of supplemental devices, such as the pointer P or robot 56. For instance, the operator may determine that the anatomical joint is sufficiently in the same position between the time registration was active and the time registration was lost. In this example, the operator can manually articulate the joint. The trackers are monitored by the navigation system 20 during joint articulation. Since joint motion is a rotational, each of the markers will move according to an arc radius that can be determined by the navigation system 20. The navigation system 20 can compare the arc radii of the markers with original arc radii data about the markers that was obtained at the time registration was active. The navigation system 20 can identify the marker for which the arc radius data is different from before and after registration was lost. The identified marker, therefore, must be part of the tracker that has experienced displacement causing the error condition.

In another example, an IR reflective marker, such as a sticker, can be rigidly placed on the anatomy or any other object rigidly attached to the anatomy, such as an anatomy holder, anatomy wrapping, or the like. The navigation system 20 can determine the position of the IR reflective marker relative to each of the markers in the tracker setup. From these distances, and the original geometry of the tracker setup, the navigation system 20 can then determine which tracker is displaced from the original geometry.

In yet another example, the navigation system 20 can utilize machine vision (e.g., by using video camera 41) to measure distances from each marker in the tracker setup to an anatomical landmark. From these distances, and the original geometry of the tracker setup, the navigation system 20 can then determine which tracker is displaced from the original geometry.

The techniques described above identify which tracker was displaced when such information is unknown to the operator or not automatically determinable by the navigation system 20. Once the navigation system 20 identifies the displaced tracker, the navigation system 20 can then proceed with guiding the operator through the registration recovery process for the identified tracker according to any suitable method, such as those described with respect to FIGS. 10 and 11. The techniques described above can be utilized individually or in combination.

According to another technique, when one of the trackers is displaced, it may be possible for the navigation system 20 to maintain a sub-optimal (less accurate) registration, instead of regarding the registration as completely lost. Such situations are possible where each tracker in the setup incudes more than two markers. Such trackers can be those from the tracker examples shown in FIGS. 4A and 4B, or any of the tracker examples of FIGS. 5-8 which are modified to include more than two markers. Having three or more markers on each tracker provides the navigation system 20 with both position and orientation information each the tracker. This enables each tracker to stand alone in preserving registration. In such configurations, even if registration is partially compromised due to displacement of one tracker, the navigation system 20 can maintain registration based on the remaining three or more markers of the originally located (non-displaced) tracker. This technique may be utilized as one option instead of repeating the full registration process or performing registration recovery.

Although the accuracy of registration will likely be less than the accuracy of registration based on both trackers, the navigation system 20 can take measures to ensure that the registration is acceptable given certain conditions. For example, the navigation system 20 can store or determine a registration accuracy tolerance required for steps of a surgical procedure. If one tracker is displaced, the navigation system 20 can monitor what step in the surgical procedure is being performed and assess the registration accuracy tolerance for the given step. If the tolerance is acceptable for the given step, the navigation system 20 can proceed with registration based on the non-displaced tracker. The navigation system 20 can notify the operator, using any appropriate technique or message, that registration is currently based on one tracker or that registration accuracy has decreased. If the navigation system 20 determines that full registration accuracy is needed for another step in the surgical procedure (e.g., a step requiring a high degree of registration accuracy), the navigation system 20 can notify the operator to repeat the full registration process or perform registration recovery, using any of the techniques described above. In other examples, the registration accuracy based only on one tracker may be sufficient for all steps of the surgical procedure such that the above analysis is not required by the navigation system 20.

A further capability of the navigation system 20 is the ability to recover registration computationally, without the need to guide the operator to mechanically manipulate the displaced tracker to the original geometry of the tracker setup. In one example, a tracker may be displaced after registration yet still detectable by the navigation system 20. A less accurate registration can still be temporarily maintained because of the non-displaced tracker remaining in its original state from the time of registration. While maintaining this registration, the navigation system 20 can determine the displaced pose of the tracker, i.e., because the displaced tracker is still detectable. The navigation system 20 can then compare the displaced pose of the tracker relative to the original pose of the tracker at the time of registration. From this comparison, the navigation system 20 can update the geometry of the tracker setup to account for the difference. For example, the original geometry of the tracker setup can be modified to account for the displaced pose of the tracker. Alternatively, the navigation system 20 can generate a new geometry of the tracker setup that replaces the old geometry. In either instance, the navigation system 20 is able to fully recover multiple tracker registration without losing registration capability in the process. This process can be performed computationally by the navigation system 20 without operator knowledge or intervention in adjusting the displaced tracker. Furthermore, the navigation system 20 can provide notifications or status updates about this type of registration recovery to the user, according to any suitable technique.

Several examples have been discussed in the foregoing description. However, the examples discussed herein are not intended to be exhaustive or limit the invention to any particular form. The terminology that has been used is intended to be in the nature of words of description rather than of limitation. Many modifications and variations are possible in light of the above teachings and the invention may be practiced otherwise than as specifically described.

The invention claimed is:

1. A method for operating a navigation system usable with a robotic manipulator and a manipulator controller configured to control the robotic manipulator, the navigation system comprising a first tracker support affixed to a rigid object and a first plurality of trackable elements secured to the first tracker support, a second tracker support affixed to the rigid object and a second plurality of trackable elements secured to the second tracker support, the first tracker support and the second tracker support adapted to be independently secured to the rigid object and separated by a distance, the navigation system comprising a localizer configured to track the first and second plurality of trackable elements, the method comprising the navigation system:
defining a tracking arrangement to be tracked based on a combination of the first and second plurality of trackable elements;
registering a geometry of the tracking arrangement relative to the rigid object;
tracking the rigid object by detecting the registered geometry of the tracking arrangement;
identifying a condition wherein at least one trackable element has been displaced relative to the registered geometry and the displacement of the at least one trackable element is not a candidate for recovering registration of the registered geometry; and
in response to identifying the condition, generating an instruction to the manipulator controller for interrupting operation of the robotic manipulator.

2. The method of claim 1, wherein generating the instruction to the manipulator controller further comprises the navigation system generating the instruction for causing the robotic manipulator to stop motion.

3. The method of claim 1, wherein generating the instruction to the manipulator controller further comprises the navigation system generating the instruction for causing the robotic manipulator to move away from a surgical object.

4. The method of claim 1, wherein the rigid object is a bone and the robotic manipulator is configured to support and move a surgical tool including an energy applicator to manipulate the bone, and further comprising the navigation system:
tracking the robotic manipulator to determine a relationship between the energy applicator and the bone.

5. The method of claim 4, further comprising the navigation system:
generating a second instruction to use the robotic manipulator to touch an anatomical landmark of the bone with the energy applicator;
registering a position of the anatomical landmark; and
identifying, based on the registered position of the anatomical landmark, the at least one trackable element that has been displaced relative to the registered geometry.

6. The method of claim 1, further comprising the navigation system:
evaluating an amount of displacement of the at least one trackable element relative to a predetermined displacement threshold or tolerance to determine whether recovering registration of the registered geometry is possible by manipulating the at least one displaced trackable element to return to the registered geometry of the tracking arrangement;
determining that recovering registration is not possible based on the evaluating the amount of displacement; and
in response, generating a notification indicating that recovering registration is not possible or that a complete re-registration is required.

7. The method of claim 1, wherein the first plurality of trackable elements comprises two or fewer trackable elements and the second plurality of trackable elements comprises two or fewer trackable elements, and further comprising the navigation system:
defining the tracking arrangement to be tracked based on a combination of the two or fewer trackable elements of the first plurality and the two or fewer trackable elements of the second plurality.

8. A method for operating a surgical system comprising navigation system, a robotic manipulator, and a manipulator controller, the navigation system comprising a first tracker support affixed to a rigid object and a first plurality of trackable elements secured to the first tracker support, a second tracker support affixed to the rigid object and a second plurality of trackable elements secured to the second tracker support, the first tracker support and the second tracker support adapted to be independently secured to the rigid object and separated by a distance, the navigation system comprising a localizer configured to track the first and second plurality of trackable elements, the method comprising:
defining, with the navigation system, a tracking arrangement to be tracked based on a combination of the first and second plurality of trackable elements;
registering, with the navigation system, a geometry of the tracking arrangement relative to the rigid object;
tracking, with the navigation system, the rigid object by detecting the registered geometry of the tracking arrangement;
controlling, with the manipulator controller, operation of the robotic manipulator;
identifying, with the navigation system, a condition wherein at least one trackable element has been displaced relative to the registered geometry and the displacement of the at least one trackable element is not a candidate for recovering registration of the of the registered geometry;
in response to identifying the condition, generating, with the navigation system, an instruction and communicating the instruction to the manipulator controller; and
in response to receiving the instruction from the navigation system, interrupting, with the manipulator controller, operation of the robotic manipulator.

9. The method of claim 8, wherein interrupting, with the manipulator controller, operation of the robotic manipulator further comprises stopping motion of the robotic manipulator.

10. The method of claim 8, wherein interrupting, with the manipulator controller, operation of the robotic manipulator further comprises controlling the robotic manipulator to move away from a surgical object.

11. The method of claim 8, wherein the rigid object is a bone and the robotic manipulator is configured to support and move a surgical tool including an energy applicator to manipulate the bone, and further comprising:

tracking, with the navigation system, the robotic manipulator to determine a relationship between the energy applicator and the bone.

12. The method of claim 11, further comprising:

generating, with the navigation system, a second instruction to use the robotic manipulator to touch an anatomical landmark of the bone with the energy applicator;

controlling, with the manipulator controller, operation of the robotic manipulator to facilitate touching the anatomical landmark of the bone with the energy applicator;

registering, with the navigation system, a position of the anatomical landmark touched by the energy applicator; and identifying, with the navigation system, and based on the registered position of the anatomical landmark, the at least one trackable element that has been displaced relative to the registered geometry.

13. The method of claim 11, further comprising the navigation system:

evaluating an amount of displacement of the at least one trackable element relative to a predetermined displacement threshold or tolerance to determine whether recovering registration of the registered geometry is possible by manipulating the at least one displaced trackable element to return to the registered geometry of the tracking arrangement;

determining that recovering registration is not possible based on the evaluating the amount of displacement; and in response, generating a notification indicating that recovering registration is not possible or that a complete re-registration is required.

* * * * *